(12) United States Patent
Godin

(10) Patent No.: US 8,669,292 B2
(45) Date of Patent: *Mar. 11, 2014

(54) THERAPEUTIC FORMULATION

(75) Inventor: Jerome Godin, Hialeah, FL (US)

(73) Assignee: Orion Therapeutics, LLC, Troy, MI (US)

( * ) Notice: Subject to any disclaimer, the term of this patent is extended or adjusted under 35 U.S.C. 154(b) by 948 days.

This patent is subject to a terminal disclaimer.

(21) Appl. No.: 12/425,574

(22) Filed: Apr. 17, 2009

(65) Prior Publication Data

US 2009/0285864 A1    Nov. 19, 2009

Related U.S. Application Data

(63) Continuation-in-part of application No. 12/130,436, filed on May 30, 2008, now Pat. No. 8,501,820, which is a continuation of application No. 11/317,534, filed on Dec. 23, 2005, now Pat. No. 7,537,774.

(51) Int. Cl.
*A01N 35/00* (2006.01)
*A61K 31/12* (2006.01)
*A01N 31/08* (2006.01)
*A61K 31/05* (2006.01)
*A01N 31/14* (2006.01)
*A61K 31/075* (2006.01)
*A01N 43/08* (2006.01)
*A61K 31/34* (2006.01)

(52) U.S. Cl.
USPC ............ 514/690; 514/731; 514/721; 514/461

(58) Field of Classification Search
USPC .................. 514/690, 731, 721, 461
See application file for complete search history.

(56) References Cited

U.S. PATENT DOCUMENTS

| 5,536,848 | A | * | 7/1996 | McLaughlin et al. | ........ 549/320 |
| 6,190,591 | B1 | * | 2/2001 | van Lengerich | .............. 264/141 |
| 6,569,857 | B1 | * | 5/2003 | Hermelin et al. | ............. 514/249 |
| 2002/0119928 | A1 | * | 8/2002 | McAnalley | ...................... 514/12 |
| 2002/0151599 | A1 | * | 10/2002 | Buchholz et al. | ............. 514/685 |
| 2003/0220294 | A1 | * | 11/2003 | Wallace et al. | ................. 514/58 |

OTHER PUBLICATIONS

Cantron promotional material, Aug. 1, 2001, pp. 5-6.*
Kelly et al. "Healing CancerThe Top 12 Non-Toxic Cancer Treatments to Help You Beat Cancer", The London Press, Jan. 2005, pp. 90-98.*
Nakamura, Seiichi "The effects of oral administration of catechol in mice" Osaka-furitsu Koshu Eisei Kenkyusho Kenkyu Hokoku, Rodo Eisei Hen, 1981, vol. 19, pp. 33-37. Abstract provided, paper ordered.*

* cited by examiner

*Primary Examiner* — Kendra D Carter
(74) *Attorney, Agent, or Firm* — The Weintraub Group, P.L.C.

(57) ABSTRACT

The invention provides compositions and formulations comprising catechol and/or acetogenins and various combinations thereof; including various combinations with other ingredients including botanical preparations containing acetogenin, an extract of green tea or a therapeutically active flavanoid contained in green tea; and one or more quinones. The invention includes a pharmaceutical composition including a salt of rhodizonic acid, an OH anion-generating base, a non-toxic acid, a quinone, a salt-containing sulfite, catechol and optionally, an acetogenin and an extract of green tea. The compositions and formulations demonstrate positive effects against a broad variety of cancer, autoimmune diseases, viruses and provides antioxidant protection against peroxyl hydrophilic, peroxyl lipophilic, hydroxyl, peroxynitrite and super oxide radicals. The compositions and formulations can be used for nutritional and nutraceutical uses, and used as dietary supplements.

6 Claims, 6 Drawing Sheets

| Material | Peroxy | Hydroxyl | Superoxide | |
|---|---|---|---|---|
| Vitamin E: 400 IU | 75 | 1125 | 32 | 1125 capsules |
| Vitamin C: 8 oz glass OJ | 2550 | * | * | 2550 glasses |
| Brocolli: Raw portion | 11 | 628 | 11 | 628 portions |
| α-Lipoic acid | 249 | 148 | 13 | 249 capsules |
| Grapeseed: 60 mg | 3 | 307 | 43 | 307 capsules |
| Green Tea Extract | 15 | 8 | 15 | 15 capsules |

FIG. 1

THERAPEUTIC FORMULATION

This application claims the benefit of, and is a continuation in part of, U.S. application Ser. No. 12/130,436, filed May 30, 2008, which is a continuation of U.S. application Ser. No. 11/317,534, filed Dec. 23, 2005, the contents each of which applications are hereby incorporated by reference.

BACKGROUND AND SUMMARY OF THE INVENTION

I. Field of the Invention

The present invention generally relates to therapeutic compositions and formulations with catechol. More particularly, the present invention relates to an oral medicament, a dietary supplement, a nutritional supplement, a food supplement, a food additive, a pharmaceutical, a nutraceutical, or nutratherapeutical formulations that include antioxidant, anticancer, antiviral and anti-rheumatic properties. The compositions and formulations demonstrate positive effects against a broad variety of cancers, autoimmune and rheumatological diseases, and provide antioxidant protection against peroxyl radicals of both the hydrophillic and the lipophilic types, hydroxyl radicals, peroxynitrite radicals and super oxide radicals.

II. Description of the Relevant Art

Cancer is one of the leading causes of death and incidences of this devastating disease are on the rise all over the world virtually afflicting every family. Attempts have been made to provide a nutra-therapeutical chemotherapeutic agent with selective activity against a broad variety of cancer cells, without the known side effects associated with orthodox chemotherapeutic agents. The proponents of these attempts believed that the known formulas for such a nutratherapeutical possessed such therapeutic properties. Furthermore, it was believed that a multitude of active ingredients existing in a necessary and precise ratio was the source of the purported anticancer activity. However, NCI, FDA and ACS, have determined that the known compositions had no effect against cancer.

Autoimmune disease or rheumatoid disorder is a pathological condition, in which a patient's normal antibodies no longer recognize its own tissues as self; and thereby attacks and breaks down these tissues. A high rheumatoid factor may lead to autoimmune and rheumatoid diseases, which diseases include lupus, erythematosus, rheumatoid arthritis, rheumatism, scleroderma, gout, polymyalgia rheumatica, fibromyalgia, ankylosing spondylitis, and osteoarthritis.

It is well known that free radicals are chemically reactive molecules that damage cellular structure and function. Free radicals are oxidants that damage and destroy healthy cells. Oxygen-based free radicals include peroxyls ($ROO^-$) of the water soluble (hydrophilic) and fat soluble (lipophilic) types, superoxide anions ($O_2^-$), peroxynitrites ($ONNO^-$) and hydroxyls ($—OH$). Sources of free radicals include ultraviolet radiation, carcinogens, and high-fat processed foods. It is also known that physical stress and even normal cell function in the production of energy are both sources for the creation and release of free radicals. A broad variety of disease states have been linked to the presence of free radicals, including arthritis, cancer, heart dysfunction, atherosclerosis, hyperoxia, stroke, cataractogenesis, retinal damage, liver injury, sexual dysfunction, periodontis, vasospasms, dermatitis, and asthma.

In response to the overwhelming presence of oxygen-based free radicals in our natural environment, attention has focused on antioxidants, compounds that can inhibit the cellular damage caused by free radicals. Natural sources of antioxidants are known and include vitamins C and E, broccoli, alpha-Lipoic acid, grapeseed, and green tea extract. While offering an avenue to obtaining the positive effects of antioxidants, the dosages of these natural foods needed to offset the oxidants is extremely high.

Attempts have also been made to provide concentrated antioxidants as a dietary supplement, a food supplement, a nutritional supplement, a food additive, a pharmaceutical, a nutraceutical, or a nutra-therapeutical according to various formulations; which contain antioxidant, anticancer, anti-viral and anti-rheumatoid properties. Each of these formulations included tetrahydroxy-1,4-quinone ($C_6H_4O_6$) (hereinafter referred to occasionally as "THQ") (in its free form and its sulfited form), croconic acid (in its free form and its sulfited form), and catechol (pyrocatechol) as active ingredients. These formulations have gone by various names, including "Entelev®," "Cantron®" (in three versions), "Cancell®," and "Protocel®" (in three versions). Perhaps the best known of these early attempts at providing an effective anti-cancer, antioxidant, anti-rheumatic and anti-viral formulation is the "Cantron®" composition which had, in addition to catechol, varied amounts of croconic acid (in its free form and its sulfited form), THQ (in its free form and its sulfited form) and rhodozonic acid, the latter converting in part to croconic acid (in its free form and its sulfited form) during the formulation process. Various additional ingredients to these formulations include sulfur, sodium, copper, potassium, triquinoyl, leuconic acid, hexahydrabenzene and traces of inositol.

While providing some improvement in the state of the art, these formulations have not proven either fully effective or completely desirable. These shortcomings include unmanageable and inadequate dosing requirements, undesirable physical characteristics of the composition, and safety issues related to the manufacturing process.

Dosage management has been a problem with these compositions in that the liquid of known formulations needed to be four to five times per day. Furthermore, new findings described herein indicate optimum dosage requirements are now every 1-2 hours; an extremely difficult schedule to follow even under the best of circumstances.

The physical characteristics of known formulations also make use of these compositions problematic. Specifically, the known compositions are designed to be orally ingested. However, the oral liquid has an extremely foul metallic taste and often burns or irritates mouth tissues. Users historically found the composition unappetizing, this problem being compounded by the user's need to consume the composition four or five times daily or optimally every one to two hours. Some users find the taste so unappealing that it causes nausea in many instances. Nausea is an undesirable characteristic even in the best of circumstances but even more undesirable for cancer patients who already may be exhibiting nausea due to the nature of the illness of from ingesting standard chemotherapeutic agents. Nine out of ten users abandon use of the known composition as a result of the adverse taste despite facing severe health challenges and in dire need of treatment. Virtually no person is willing to take this formulation on a prophylactic basis because of taste issues. This not only renders a situation with poor patient compliance but it also makes for a poor product in the marketplace.

Beyond taste, the dark black liquid of known compositions is itself visually unappealing. The color of the known compositions is known to stain teeth, clothing, furniture, and carpeting. The stains on clothing, furniture and carpeting are permanent as well as in the case of porous teeth. The problem is further compounded by the difficulty of traveling with these bulky liquid compositions. The container top is subject to loosening because of the gases naturally generated by the composition and causes leakage which is problematic for shipping or traveling because the dark black liquid destroys all other products contained in a shipping container or in baggage whereby it permanently damages clothing and other valuable items.

Of concern to manufacturers is the production process itself. The manufacturing procedure of the formula is extremely dangerous as the oxidation process to create the various compounds causes the release of a highly toxic and acidic gas. Experience has taught that the larger the volume of product being produced, the more dangerous the chemical reaction. So dangerous is the manufacturing procedure for known compositions that production on a large scale may lead to injury or death, which is the reason that previous manufacturing has been done on a small scale only. Because of the level of pernicious nitric fumes generated, even protective wear that would ordinarily be effective (such as gas masks) fail to protect the operator. Furthermore, experience has shown that stove wiring, fan motors, vacuum motors and general laboratory equipment must be renewed constantly and at considerable expense due to the presence of these acidic gases. In addition, laboratory cleanliness is all but impossible to maintain given the presence of these gases, resulting in stained walls, floors and furniture. So extreme is the problem that to maintain laboratory cleanliness at even the most rudimentary level the walls must be recoated with paint after the production of each batch. Given these problems, FDA or regulatory authority inspection compliance has been problematic.

Beyond the difficulties associated with the production of known compositions, the known compositions have a variety of demonstrable shortcomings. First, prior compositions fail to produce an optimum effect in that they do not utilize the most effective administration methods or dosages. Second, known compositions are unsafe to manufacture in any significant quantity. Third, known compositions have a black, tarry appearance and are unappealing to the user in appearance. Fourth, known compositions are unappealing to the user in taste.

Accordingly, new compositions and improved formulations that demonstrate higher antioxidant characteristics on the major oxygen related species of free radicals, increased efficacy against a broad variety of cancers, autoimmune diseases such as lupus and rheumatoid arthritis and a broad array of viruses (including for example, the AIDS virus) while allowing safe manufacture and appeal to the user are desired.

SUMMARY OF THE INVENTION

In one aspect, the invention provides a composition for the treatment of cancer, rheumatic disorder, or autoimmune disorder; or for scavenging free radicals, comprising a therapeutically effective amount of a chemical having the form

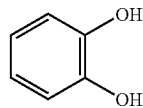

wherein the composition is formulated as a tablet, a capsule, a time release tablet, a time release capsule; a time release pellet; a sublingual tablet; a gel capsule; a microencapsulation; a transdermal delivery formulation; a transdermal gel; a transdermal patch; a sterile solution; a sterile solution prepared for use as an intramuscular or subcutaneous injection, for use as a direct injection into a targeted site, or for intravenous administration; a solution prepared for rectal administration; a solution prepared for administration through a gastric feeding tube or duodenal feeding tube; a suppository for rectal administration; a liquid for oral consumption prepared as a solution or an elixir; a topical cream; a gel; a lotion; a tincture; a syrup; an emulsion; or a suspension; except that wherein the composition is formulated as a liquid for oral consumption prepared as a solution or an elixir, catechol is the only active ingredient.

In a second aspect, the invention provides a composition for the treatment of cancer, rheumatic disorder, or autoimmune disorder; or for scavenging free radicals, the composition consisting essentially of therapeutically effective amounts of a first ingredient consisting of a chemical having the form:

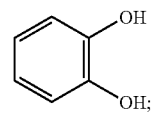

and at least one second ingredient selected from the group consisting of: an anti-neoplastic in the form of acetogenin or a botanical preparation that comprises an anti-neoplastic in the form of acetogenin; an extract of green tea or a therapeutically active flavanoid contained in green tea; and a quinone selected from the group consisting of tetrahydroxyquinone and sulfites of tetrahydroxyquinone.

In a third aspect, the invention provides a composition for the treatment of cancer, rheumatic disorder, or autoimmune disorder; or for scavenging free radicals, the composition consisting essentially of therapeutically effective amounts of a chemical having the form: an anti-neoplastic in the form of acetogenin; an extract of green tea; and a quinone selected from the group consisting of tetrahydroxyquinone and sulfites of tetrahydroxyquinone.

In a fourth aspect, the invention provides a composition for the treatment of cancer, rheumatic disorder, or autoimmune disorder; or for scavenging free radicals, the composition comprising therapeutically effective amounts of a first ingredient consisting of a chemical having the form:

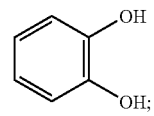

and at least one second ingredient selected from the group consisting of:
   a) an anti-neoplastic in the form of acetogenin or a botanical preparation that comprises an anti-neoplastic in the form of acetogenin;
   b) an extract of green tea or a therapeutically active flavanoid contained in green tea; and
   c) a quinone selected from the group consisting of tetrahydroxyquinone and sulfites of tetrahydroxyquinone;
wherein the composition is formulated as a dry powder or granules, a tablet, a capsule, a time release tablet, a time release capsule; a time release pellet; a sublingual tablet; a gel capsule; a microencapsulation; a transdermal delivery formulation; a transdermal gel; a transdermal patch; a sterile solution; a sterile solution prepared for use as an intramuscular or subcutaneous injection, for use as a direct injection into a targeted site, or for intravenous administration; a solution prepared for rectal administration; a solution prepared for administration through a gastric feeding tube or duodenal feeding tube; a suppository for rectal administration; a liquid for oral consumption prepared as a solution or an elixir; a topical cream; a gel; a lotion; a tincture; a syrup; an emulsion; or a suspension;

except that wherein the composition does not comprise at least one second ingredient selected from the group consisting of: b) and c), then the composition is not formulated as a liquid for oral consumption prepared as a solution or an elixir.

In a fifth aspect, the invention provides composition for the treatment of cancer, rheumatic disorder, or autoimmune disorder; or for scavenging free radicals, the composition comprising therapeutically effective amounts of a chemical having the form

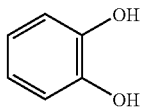

and at least one quinone selected from the group consisting of tetrahydroxyquinone, hexahydrabenzene, rhodizonic acid, triquinol, triquinoyl, leuconic acid and a sulfite of tetrahydroxyquinone, hexahydrabenzene, rhodizonic acid, triquinol, triquinoyl or leuconic acid; and an acid selected from the group consisting of croconic acid and a sulfite of croconic acid; wherein the composition is formulated as a dry powder or granules, a tablet, a capsule, a time release tablet, a time release capsule; a time release pellet, a time release pellet; a sublingual tablet; a gel capsule; a microencapsulation; a transdermal delivery formulation; a transdermal gel; a transdermal patch; a sterile solution; a sterile solution prepared for use as an intramuscular or subcutaneous injection, for use as a direct injection into a targeted site, or for intravenous administration; a solution prepared for rectal administration; a solution prepared for administration through a gastric feeding tube or duodenal feeding tube; a suppository for rectal administration; a topical cream; a gel; a lotion; a tincture; a syrup; an emulsion; or a suspension.

In a sixth aspect, the invention provides a composition for the treatment of cancer, rheumatic disorder, or autoimmune disorder; or for scavenging free radicals, the composition comprising a therapeutically effective amount of an antineoplastic in the form of acetogenin, wherein the composition is formulated as a time release tablet, a time release capsule; a time release pellet, a transdermal delivery formulation; a transdermal gel; a transdermal patch; a sterile solution; a sterile solution prepared for use as an intramuscular or subcutaneous injection, for use as a direct injection into a targeted site, or for intravenous administration; a solution prepared for rectal administration; a solution prepared for administration through a gastric feeding tube or duodenal feeding tube; or a suppository for rectal administration.

In a further aspect, the invention provides methods for treatment of cancer, rheumatic disorder, or autoimmune disorder; or for scavenging free radicals in a mammal including a human, comprising administering a composition set forth in the first, second, third, fourth, fifth, or sixth aspect of the invention; or a combination thereof.

In a particular aspect, the invention provides a method for treatment of cancer, rheumatic disorder, or autoimmune disorder; or for scavenging free radicals in a mammal including a human, comprising administering a therapeutically effective amount of a chemical having the form

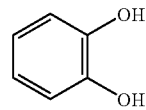

wherein the composition is formulated as a tablet, a capsule, a time release tablet, a time release capsule; a time release pellet; a sublingual tablet; a gel capsule; a microencapsulation; a transdermal delivery formulation; a transdermal gel; a transdermal patch; a sterile solution; a sterile solution prepared for use as an intramuscular or subcutaneous injection, for use as a direct injection into a targeted site, or for intravenous administration; a solution prepared for rectal administration; a solution prepared for administration through a gastric feeding tube or duodenal feeding tube; a suppository for rectal administration; a liquid for oral consumption prepared as a solution or an elixir; a topical cream; a gel; a lotion; a tincture; a syrup; an emulsion; or a suspension.

with that wherein said composition is formulated as a liquid for oral consumption prepared as a solution or an elixir, catechol is the only active ingredient.

The invention further encompasses methods for nutritional supplementation, dietary supplementation, food supplementation, nutraceutical administration or nutra-therapeutical administration in a subject including a human, comprising orally administering a composition set forth in the first, second, third, fourth, fifth, or sixth aspect of the invention; or a combination thereof.

The invention further provides the described compositions formulated as time release pellets, and/or dry powder or granules; as described in further detail below. Particular embodiments of the present invention include a food preparation, a time release pellet, and/or dry powder or granules set forth in various formulations of the inventive compositions. Thus, it is recognized that the present composition can be administered as a food or pet food additive, and the invention encompasses such food preparations comprising the time release pellets and/or dry powder or granules. The invention further encompasses methods of administering the food preparations of the present invention to a subject.

Particular compositions of the present invention generally include any therapeutically effective combination of a salt of rhodizonic acid and an OH anion-generating base (resulting in croconic acid), a non-toxic acid, a quinone, a salt-containing sulfite, catechol, an acetogenin, and an extract of green tea or any of the therapeutically effective components of green tea including catechin, epicatechin, epicatechin gallate, epigallocatechin, epigallocatechin gallate or other similar compounds such as flavone, myricetin, quercitin, or rutin. The invention includes inventive administrative forms (formulations) necessary to improve efficacy, dosage compliance, convenience, aesthetics and appeal.

The compositions of the present invention overcomes the failings of known compositions and methods of disease treatments by providing a composition that is high in antioxidants, is safe to produce, and is adaptable to administration to a patient without the undesirable appeal problems associated with the known compositions and methods. The compositions are more efficacious against disease states and health damaging species of free radicals.

The compositions can be characterized as an oral medicament, a nutritional supplement, a dietary supplement, a food supplement, a food additive, a pharmaceutical, a nutraceutical, or a nutratherapeutical composition, and the invention encompasses providing the compositions as such.

The compositions of the present invention are strong antioxidants. They are also effective against a broad variety of cancer(s), autoimmune and rheumatoid diseases such as lupus and rheumatoid arthritis and many viruses. The present composition is herein shown to be an effective antioxidant that works on the major forms of the oxygen-related species of free radicals, including the peroxyl (hydrophilic and lipophilic), hydroxyl, peroxynitrite and super oxide radicals. It is also believed that the compositions of the present invention has utility in reducing the side effects of radiation therapy and chemotherapy, as well as in radio-sensitizing tumors; thus improving the efficacy of radiation therapy.

The compositions of the present invention also overcome the problems commonly associated with the production of the known nutratherapeutical compositions by the effective elimination of the noxious fumes. This results in improved laboratory conditions and ease of maintenance of proper conditions. The invention encompasses methods of producing the inventive compositions described herein, including the methods particularly set forth and/or provided below by way of example.

The present invention also improves the efficacy of the known nutratherapeutical formulas against tumors, by providing chronic cytotoxic dosing of tumors, and by providing a more consistent supply of antioxidants in the bloodstream, thereby providing a more effective in-vivo method of destroying the pernicious oxygen species of free radicals that are implicated in over 50 disease states.

As a further improvement over the art, the various compositions of the present invention may achieve superior efficacies without the use of such components as copper, potassium, triquinoyl, leuconic acid, hexahydrabenzene and rhodozonic acid. The absence of these components, while improving the effectiveness of the various compositions of the present invention, further supports the effectiveness of the unique approach described herein. By avoiding such extra components, possible adverse patient reactions and cost can be reduced. Improvement is also achieved by adding other synergistic components, which yield superior antioxidant and anticancer properties such as acetogenins, an extract of green tea which is high in flavanoids such as catechin, epicatechin, epicatechin gallate, epigallocatechin, epigallocatechin gallate or other similar compounds such as flavone, myricetin, quercitin, or rutin.

Whether comprised of the identical ingredients of the known composition Cantron or comprised of the superior components of the new compositions described herein, the new administrative forms (formulations) of the invention represent a significant improvement over the oral liquid form that has been solely employed for decades as they improve efficacy, dosage compliance, convenience, aesthetics and appeal by removing the characteristic adverse taste, burning of mouth tissues and other such disadvantages. The new forms change the characteristics of the known composition dramatically and these vastly superior properties represent a new and significant invention.

Other advantages and features of the present invention will become apparent from the following detailed description and appended claims.

DESCRIPTION OF THE DRAWINGS

FIG. 1 is a graph showing a comparison of the antioxidant effect of the formula of the present invention compared with antioxidants obtained from foods and pure vitamin sources.

DETAILED DESCRIPTION OF THE PREFERRED EMBODIMENTS

Figure 2:
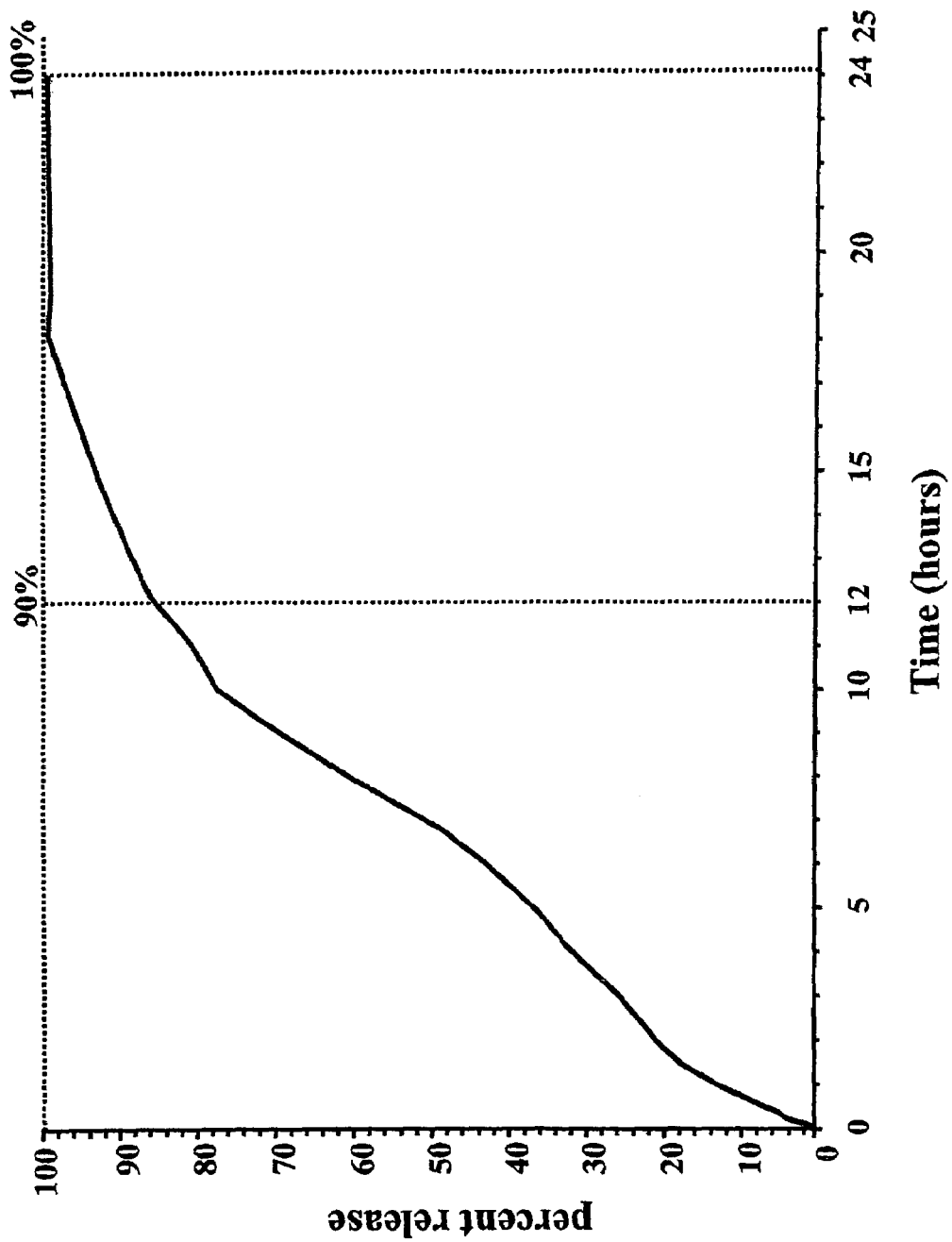
FIG. 2 is a graph illustrating the time release kinetics of the composition according to the present invention.

The compositions and methods of treatment of the present invention are set forth below. However, it is envisioned that alternate compositions of the present invention may be adopted without deviating from the present invention. Particular embodiments of the invention are set forth below.

The Compositions and Methods

In one aspect, the invention provides a composition for the treatment of cancer, rheumatic disorder, or autoimmune disorder; or for scavenging free radicals, comprising a therapeutically effective amount of a chemical having the form:

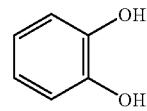

wherein the composition is formulated as a tablet, a capsule, a time release tablet, a time release capsule; a time release pellet; a sublingual tablet; a gel capsule; a microencapsulation; a transdermal delivery formulation; a transdermal gel; a transdermal patch; a sterile solution; a sterile solution prepared for use as an intramuscular or subcutaneous injection, for use as a direct injection into a targeted site, or for intravenous administration; a solution prepared for rectal administration; a solution prepared for administration through a gastric feeding tube or duodenal feeding tube; a suppository for rectal administration; a liquid for oral consumption prepared as a solution or an elixir; a topical cream; a gel; a lotion; a tincture; a syrup; an emulsion; or a suspension; except that wherein the composition is formulated as a liquid for oral consumption prepared as a solution or an elixir, catechol is the only active ingredient.

In one embodiment of the present invention, the cancer is at least one cancer selected from the group consisting of a sarcoma, carcinoma, adenocarcinoma, glioma, glioblastoma, melanoma, leukemia, colon cancer, lung cancer, breast cancer, prostate cancer, ovarian cancer, brain cancer, pancreatic cancer, or liver cancer; the rheumatic disorder is at least one rheumatic disorder selected from the group consisting of rheumatoid arthritis, rheumatism, polymyalgia rheumatica, osteoarthritis, and fibromyalgia; the autoimmune disorder is at least one autoimmune disorder selected from the group consisting of lupus, erythematosus, and scleroderma; and the free radical is at least one free radical selected from the group consisting of lipophilic peroxyl radicals, hydrophilic peroxyl radicals, hydroxyl radicals, peroxynitrite radicals, and superoxide anions.

In another, the composition further comprises a pharmaceutically acceptable carrier or an inert carrier.

In another, the composition is further formulated for nutritional supplementation, dietary supplementation, food supplementation, nutraceutical administration or nutra-therapeutical administration; and formulated as a tablet, a capsule, a time release tablet, a time release capsule, a time release pellet, a sublingual tablet, a gel capsule, a microencapsulation, a liquid for oral consumption prepared as a solution or an elixir, a tincture, a syrup, an emulsion, or a suspension.

In another, the composition is further formulated as a gel, lotion, tincture, syrup, emulsion, or suspension.

In another, the composition is further formulated as an oral liquid, topical cream, gel, lotion, elixir, tincture, syrup, emulsion, or suspension wherein catechol is the only active ingredient.

Another embodiment of the present invention is a food preparation comprising the time release pellet set forth above in this aspect of the invention, and at least one food ingredient or at least one pet food ingredient. Thus, it is recognized that the present composition can be administered as a food or pet food additive, and the invention encompasses such food preparations comprising the time release pellet of the present invention. The invention further encompasses methods of administering the food preparations of the present invention to a subject.

In another embodiment of the present invention, the composition further comprises a quinone selected from the group consisting of tetrahydroxyquinone and sulfites of tetrahydroxyquinone; an acid selected from the group consisting of croconic acid and sulfites of croconic acid; or a quinone selected from the group consisting of tetrahydroxyquinone and sulfites of tetrahydroxyquinone, and an acid selected from the group consisting of croconic acid and sulfites of croconic acid.

In another, the composition further comprises a therapeutically effective amount of an anti-neoplastic in the form of acetogenin, In another, the composition further comprises a quinone selected from the group consisting of tetrahydroxyquinone and sulfites of tetrahydroxyquinone;
an acid selected from the group consisting of croconic acid and sulfites of croconic acid; or a quinone selected from the group consisting of tetrahydroxyquinone and sulfites of tetrahydroxyquinone, and an acid selected from the group consisting of croconic acid and sulfites of croconic acid; and further comprises a therapeutically effective amount of an anti-neoplastic in the form of acetogenin, In another, the composition further comprises a botanical preparation that comprises a therapeutically effective amount of an anti-neoplastic in the form of acetogenin.

In another, the composition further comprises a quinone selected from the group consisting of tetrahydroxyquinone and sulfites of tetrahydroxyquinone;
an acid selected from the group consisting of croconic acid and sulfites of croconic acid; or a quinone selected from the group consisting of tetrahydroxyquinone and sulfites of tetrahydroxyquinone, and an acid selected from the group consisting of croconic acid and sulfites of croconic acid; and further comprises a botanical preparation that comprises a therapeutically effective amount of an anti-neoplastic in the form of acetogenin.

In another, the composition further comprises a botanical preparation that comprises a therapeutically effective amount of an anti-neoplastic in the form of acetogenin; wherein said botanical preparation comprises components of Paw Paw Tree, Graviola Tree, or an extract of said components.

In another, the composition further comprises a quinone selected from the group consisting of tetrahydroxyquinone and sulfites of tetrahydroxyquinone; an acid selected from the group consisting of croconic acid and sulfites of croconic acid; or quinone selected from the group consisting of tetrahydroxyquinone and sulfites of tetrahydroxyquinone, and an acid selected from the group consisting of croconic acid and sulfites of croconic acid; and further comprises a botanical preparation that comprises a therapeutically effective amount of an anti-neoplastic in the form of acetogenin; wherein said botanical preparation comprises components of Paw Paw Tree, Graviola Tree, or an extract of said components.

In a second aspect, the invention provides a composition for the treatment of cancer, rheumatic disorder, or autoimmune disorder; or for scavenging free radicals, the composition consisting essentially of therapeutically effective amounts of a first ingredient consisting of a chemical having the form:

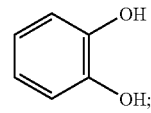

and at least one second ingredient selected from the group consisting of: an anti-neoplastic in the form of acetogenin or a botanical preparation that comprises an anti-neoplastic in the form of acetogenin; an extract of green tea or a therapeutically active flavanoid contained in green tea; and a quinone selected from the group consisting of tetrahydroxyquinone and sulfites of tetrahydroxyquinone.

In one embodiment of the present invention, the botanical preparation comprises components of at least one of Paw Paw Tree, Graviola Tree, or an extract of said components.

In another, the composition further consists essentially of at least two second ingredients selected from the group consisting of: an anti-neoplastic in the form of acetogenin or a botanical preparation that comprises an anti-neoplastic in the form of acetogenin; an extract of green tea or a therapeutically active flavanoid contained in green tea; and a quinone selected from the group consisting of tetrahydroxyquinone and sulfites of tetrahydroxyquinone.

In another, the composition further consists essentially of: an anti-neoplastic in the form of acetogenin or a botanical preparation that comprises an anti-neoplastic in the form of acetogenin, wherein said botanical preparation comprises components of at least one of Paw Paw Tree, Graviola Tree, or an extract of said components; an extract of green tea or a therapeutically active flavanoid contained in green tea; and a quinone selected from the group consisting of tetrahydroxyquinone and sulfites of tetrahydroxyquinone.

In another, the therapeutically active flavanoid is at least one of catechin, epicatechin, epicatechin gallate, epigallocatechin, epigallocatechin gallate, flavone, myricetin, quercitin, or rutin.

In another, the cancer is at least one cancer selected from the group consisting of a sarcoma, carcinoma, adenocarcinoma, glioma, glioblastoma, melanoma, leukemia, colon cancer, lung cancer, breast cancer, prostate cancer, ovarian cancer, brain cancer, pancreatic cancer, or liver cancer; the rheumatic disorder is at least one rheumatic disorder selected from the group consisting of rheumatoid arthritis, rheumatism, polymyalgia rheumatica, osteoarthritis, and fibromyalgia; the autoimmune disorder is at least one autoimmune disorder selected from the group consisting of lupus, erythematosus, and scleroderma; the free radical is at least one free radical selected from the group consisting of lipophilic peroxyl radicals, hydrophilic peroxyl radicals, hydroxyl radicals, peroxynitrite radicals or superoxide anions.

In another, the composition is formulated as a dry powder or granules, a tablet, a capsule, a time release tablet, a time release capsule; a time release pellet, a sublingual tablet; a gel capsule; a microencapsulation; a transdermal delivery formulation; a transdermal gel; a transdermal patch; a sterile solution; a sterile solution prepared for use as an intramuscular or subcutaneous injection, for use as a direct injection into a targeted site, or for intravenous administration; a solution prepared for rectal administration; a solution prepared for administration through a gastric feeding tube or duodenal feeding tube; or a suppository for rectal administration; a liquid for oral consumption prepared as a solution or an elixir; a topical cream; a gel; a lotion; a tincture; a syrup; an emulsion; or a suspension.

In another, the composition further comprises a pharmaceutically acceptable carrier or an inert carrier.

In another, the composition is further formulated for nutritional supplementation, dietary supplementation, food supplementation, nutraceutical administration or nutra-therapeutical administration; and formulated as a dry powder or granules, a tablet, a capsule, a time release tablet, a time release capsule; a time release pellet, a sublingual tablet, a gel capsule, a microencapsulation, a liquid for oral consumption prepared as a solution or an elixir, a tincture, a syrup, an emulsion, or a suspension.

Another embodiment of the present invention is a food preparation comprising the dry powder or granules, or the time release pellet set forth above in this second aspect of the invention, and at least one food ingredient or at least one pet food ingredient. Thus, it is recognized that the present composition can be administered as a food or pet food additive, and the invention encompasses such food preparations comprising the dry powder or granules, or the time release pellet of the present invention. The invention further encompasses methods of administering the food preparations of the present invention to a subject.

In a third aspect, the invention provides a composition for the treatment of cancer, rheumatic disorder, or autoimmune disorder; or for scavenging free radicals, the composition consisting essentially of therapeutically effective amounts of a chemical having the form:

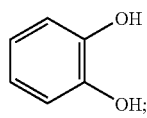

an anti-neoplastic in the form of acetogenin; an extract of green tea; and a quinone selected from the group consisting of tetrahydroxyquinone and sulfites of tetrahydroxyquinone.

In one embodiment of the present invention, the cancer is at least one cancer selected from the group consisting of a sarcoma, carcinoma, adenocarcinoma, glioma, glioblastoma, melanoma, leukemia, colon cancer, lung cancer, breast cancer, prostate cancer, ovarian cancer, brain cancer, pancreatic cancer, or liver cancer; the rheumatic disorder is at least one rheumatic disorder selected from the group consisting of rheumatoid arthritis, rheumatism, polymyalgia rheumatica, osteoarthritis, and fibromyalgia; the autoimmune disorder is at least one autoimmune disorder selected from the group consisting of lupus, erythematosus, and scleroderma; and the free radical is at least one free radical selected from the group consisting of lipophilic peroxyl radicals, hydrophilic peroxyl radicals, hydroxyl radicals, peroxynitrite radicals or superoxide anions.

In another, the composition is formulated as a dry powder or granules, a tablet, a capsule, a time release tablet, a time release capsule; a time release pellet, a sublingual tablet; a gel capsule; a microencapsulation; a transdermal delivery formulation; a transdermal gel; a transdermal patch; a sterile solution; a sterile solution prepared for use as an intramuscular or subcutaneous injection, for use as a direct injection into a targeted site, or for intravenous administration; a solution prepared for rectal administration; a solution prepared for administration through a gastric feeding tube or duodenal feeding tube; or a suppository for rectal administration; a liquid for oral consumption prepared as a solution or an elixir; a topical cream; a gel; a lotion; a tincture; a syrup; an emulsion; or a suspension.

In another, the composition is further formulated for nutritional supplementation, dietary supplementation, food supplementation, nutraceutical administration or nutra-therapeutical administration; and formulated as a dry powder or granules, a tablet, a capsule, a time release tablet, a time release capsule, a time release pellet, a sublingual tablet, a gel capsule, a microencapsulation, a liquid for oral consumption prepared as a solution or an elixir, a tincture, a syrup, an emulsion, or a suspension.

Another embodiment of the present invention is a food preparation comprising the dry powder or granules, or the time release pellet set forth above in this third aspect of the invention, and at least one food ingredient or at least one pet food ingredient. Thus, it is recognized that the present composition can be administered as a food or pet food additive, and the invention encompasses such food preparations comprising the dry powder or granules, or the time release pellet of the present invention. The invention further encompasses methods of administering the food preparations of the present invention to a subject.

In a fourth aspect, the invention provides a composition for the treatment of cancer, rheumatic disorder, or autoimmune disorder; or for scavenging free radicals, the composition comprising therapeutically effective amounts of a first ingredient consisting of a chemical having the form:

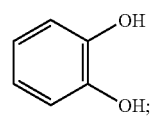

and at least one second ingredient selected from the group consisting of:
a) an anti-neoplastic in the form of acetogenin or a botanical preparation that comprises an anti-neoplastic in the form of acetogenin;

b) an extract of green tea or a therapeutically active flavanoid contained in green tea; and c) a quinone selected from the group consisting of tetrahydroxyquinone and sulfites of tetrahydroxyquinone;

wherein the composition is formulated as a dry powder or granules, a tablet, a capsule, a time release tablet, a time release capsule; a time release pellet, a sublingual tablet; a gel capsule; a microencapsulation; a transdermal delivery formulation; a transdermal gel; a transdermal patch; a sterile solution; a sterile solution prepared for use as an intramuscular or subcutaneous injection, for use as a direct injection into a targeted site, or for intravenous administration; a solution prepared for rectal administration; a solution prepared for administration through a gastric feeding tube or duodenal feeding tube; a suppository for rectal administration; a liquid for oral consumption prepared as a solution or an elixir; a topical cream; a gel; a lotion; a tincture; a syrup; an emulsion; or a suspension;

except that wherein the composition does not comprise at least one second ingredient selected from the group consisting of: b) and c), then the composition is not formulated as a liquid for oral consumption prepared as a solution or an elixir.

In one embodiment of the present invention, the botanical preparation comprises components of at least one of Paw Paw Tree, Graviola Tree, or an extract of said components.

In another, the composition further comprises at least two second ingredients selected from the group consisting of: an anti-neoplastic in the form of acetogenin, or a botanical preparation that comprises an anti-neoplastic in the form of acetogenin, wherein said botanical preparation comprises components of at least one of Paw Paw Tree, Graviola Tree, or an extract of said components; an extract of green tea or a therapeutically active flavanoid contained in green tea; and a quinone selected from the group consisting of tetrahydroxyquinone and sulfites of tetrahydroxyquinone.

In another, the composition further comprises: an anti-neoplastic in the form of acetogenin or a botanical preparation that comprises an anti-neoplastic in the form of acetogenin, wherein the botanical preparation comprises components of at least one of Paw Paw Tree, Graviola Tree, or an extract of said components; an extract of green tea or a therapeutically active flavanoid contained in green tea; and a quinone selected from the group consisting of tetrahydroxyquinone and sulfites of tetrahydroxyquinone.

In another, the therapeutically active flavanoid is at least one of catechin, epicatechin, epicatechin gallate, epigallocatechin, epigallocatechin gallate, flavone, myricetin, quercitin, or rutin.

In another, the composition further comprises a pharmaceutically acceptable carrier or an inert carrier.

In another, the composition is further formulated for nutritional supplementation, dietary supplementation, food supplementation, nutraceutical administration or nutra-therapeutical administration; and formulated as a dry powder or granules, a tablet, a capsule, a time release tablet, a time release capsule, a time release pellet, a sublingual tablet, a gel capsule, a microencapsulation, a liquid for oral consumption prepared as a solution or an elixir, a tincture; a syrup; an emulsion, or a suspension.

In another, the composition is further formulated as a topical cream, gel, lotion, tincture, syrup, emulsion, or suspension.

Another embodiment of the present invention is a food preparation comprising the dry powder or granules, or the time release pellet set forth above in this fourth aspect of the invention, and at least one food ingredient or at least one pet food ingredient. Thus, it is recognized that the present composition can be administered as a food or pet food additive, and the invention encompasses such food preparations comprising the dry powder or granules, or the time release pellet of the present invention. The invention further encompasses methods of administering the food preparations of the present invention to a subject.

In a fifth aspect, the invention provides composition for the treatment of cancer, rheumatic disorder, or autoimmune disorder; or for scavenging free radicals, the composition comprising therapeutically effective amounts of a chemical having the form

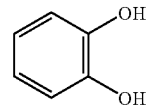

and at least one quinone selected from the group consisting of tetrahydroxyquinone, hexahydrabenzene, rhodizonic acid, triquinol, triquinoyl, leuconic acid and a sulfite of tetrahydroxyquinone, hexahydrabenzene, rhodizonic acid, triquinol, triquinoyl or leuconic acid; and an acid selected from the group consisting of croconic acid and a sulfite of croconic acid; wherein the composition is formulated as a dry powder or granules, a tablet, a capsule, a time release tablet, a time release capsule; a time release pellet, a time release pellet; a sublingual tablet; a gel capsule; a microencapsulation; a transdermal delivery formulation; a transdermal gel; a transdermal patch; a sterile solution; a sterile solution prepared for use as an intramuscular or subcutaneous injection, for use as a direct injection into a targeted site, or for intravenous administration; a solution prepared for rectal administration; a solution prepared for administration through a gastric feeding tube or duodenal feeding tube; a suppository for rectal administration; a topical cream; a gel; a lotion; a tincture; a syrup; an emulsion; or a suspension.

In one embodiment of the present invention, the composition further comprises a pharmaceutically acceptable carrier or an inert carrier.

In another, the composition is further formulated for nutritional supplementation, dietary supplementation, food supplementation, nutraceutical administration or nutra-therapeutical administration; and formulated as a dry powder or granules, a tablet, a capsule, a time release tablet, a time release capsule; a time release pellet; a sublingual tablet; a gel capsule; a microencapsulation; a tincture; a syrup; an emulsion; or a suspension.

In another, the composition is further formulated as a topical cream, gel, lotions, tincture, syrup, emulsion, or suspension;

Another embodiment of the present invention is a food preparation comprising the dry powder or granules, or the time release pellet set forth above in this fifth aspect of the invention, and at least one food ingredient or at least one pet food ingredient. Thus, it is recognized that the present composition can be administered as a food or pet food additive, and the invention encompasses such food preparations comprising the dry powder or granules, or the time release pellet of the present invention. The invention further encompasses methods of administering the food preparations of the present invention to a subject.

In another embodiment of the present invention, the composition further comprises an anti-neoplastic in the form of acetogenin, In another, the composition further comprises a botanical preparation that comprises an anti-neoplastic in the form of acetogenin, wherein the acetogenin is in a therapeutically effective amount in said composition.

In another, the composition further comprises a botanical preparation that comprises an anti-neoplastic in the form of acetogenin; wherein the acetogenin is in a therapeutically effective amount in said composition; and wherein the botanical preparation comprises components of Paw Paw Tree, Graviola Tree, or an extract of the components.

In another, the composition further comprises an extract of green tea.

In another, the composition further comprises at least one therapeutically active flavanoid contained in an extract of green tea.

In another, the composition further comprises at least one therapeutically active flavanoid contained in an extract of green tea wherein the at least one therapeutically active flavanoid is catechin, epicatechin, epicatechin gallate, epigallocatechin, epigallocatechin gallate, flavone, myricetin, quercitin, or rutin.

In another, the composition further comprises an anti-neoplastic in the form of acetogenin and an extract of green tea.

In another, the composition further comprises one or more minerals chosen from the group of potassium, sodium, copper, and sulfur.

In another, the composition further comprises trace amounts of inositol,

In another, the cancer is at least one cancer selected from the group consisting of a sarcoma, carcinoma, adenocarcinoma, glioma, glioblastoma, melanoma, leukemia, colon cancer, lung cancer, breast cancer, prostate cancer, ovarian cancer, brain cancer, pancreatic cancer, or liver cancer; wherein the rheumatic disorder is at least one rheumatic disorder selected from the group consisting of rheumatoid arthritis, rheumatism, polymyalgia rheumatica, osteoarthritis, and fibromyalgia; wherein said autoimmune disorder is at least one autoimmune disorder selected from the group consisting of lupus, erythematosus, and scleroderma; and wherein the free radical is at least one free radical selected from the group consisting of lipophilic peroxyl radicals, hydrophilic peroxyl radicals, hydroxyl radicals, peroxynitrite radicals or superoxide anions.

In a sixth aspect, the invention provides a composition for the treatment of cancer, rheumatic disorder, or autoimmune disorder; or for scavenging free radicals, the composition comprising a therapeutically effective amount of an antineoplastic in the form of acetogenin, wherein the composition is formulated as a time release tablet, a time release capsule; a time release pellet, a transdermal delivery formulation; a transdermal gel; a transdermal patch; a sterile solution; a sterile solution prepared for use as an intramuscular or subcutaneous injection, for use as a direct injection into a targeted site, or for intravenous administration; a solution prepared for rectal administration; a solution prepared for administration through a gastric feeding tube or duodenal feeding tube; or a suppository for rectal administration.

In one embodiment of the present invention, the cancer is at least one cancer selected from the group consisting of a sarcoma, carcinoma, adenocarcinoma, glioma, glioblastoma, melanoma, leukemia, colon cancer, lung cancer, breast cancer, prostate cancer, ovarian cancer, brain cancer, pancreatic cancer, or liver cancer; wherein the rheumatic disorder is at least one rheumatic disorder selected from the group consisting of rheumatoid arthritis, rheumatism, polymyalgia rheumatica, osteoarthritis, and fibromyalgia; wherein the autoimmune disorder is at least one autoimmune disorder selected from the group consisting of lupus, erythematosus, and scleroderma; and wherein the free radical is at least one free radical selected from the group consisting of lipophilic peroxyl radicals, hydrophilic peroxyl radicals, hydroxyl radicals, peroxynitrite radicals or superoxide anions.

In another, the composition further comprises a pharmaceutically acceptable carrier or an inert carrier.

In another, the composition is further formulated for nutritional supplementation, dietary supplementation, food supplementation, nutraceutical administration or nutra-therapeutical administration; and formulated as a time release tablet, a time release capsule; or a time release pellet.

In another, the composition further comprises an extract of Green Tea.

In another, the composition further comprises at least one therapeutically active flavanoid contained in an extract of green tea.

In another, the composition further comprises a quinone selected from the group consisting of tetrahydroxyquinone and sulfites of tetrahydroxyquinone.

In another, the composition further comprises a quinone selected from the group consisting of tetrahydroxyquinone and sulfites of tetrahydroxyquinone; and an extract of green tea, or at least one therapeutically active flavanoid contained in an extract of green tea wherein the at least one therapeutically active flavanoid is catechin, epicatechin, epicatechin gallate, epigallocatechin, epigallocatechin gallate, flavone, myricetin, quercitin, or rutin.

Another embodiment of the present invention is a food preparation comprising the time release pellet set forth above in this sixth aspect of the invention, and at least one food ingredient or at least one pet food ingredient. Thus, it is recognized that the present composition can be administered as a food or pet food additive, and the invention encompasses such food preparations comprising the time release pellet of the present invention. The invention further encompasses methods of administering the food preparations of the present invention to a subject.

In a further aspect, the invention provides methods for treatment of cancer, rheumatic disorder, or autoimmune disorder; or for scavenging free radicals in a mammal including a human, comprising administering a composition set forth in the first, second, third, fourth, fifth, or sixth aspect of the invention; or a combination thereof.

In a particular aspect, the invention provides a method for treatment of cancer, rheumatic disorder, or autoimmune disorder; or for scavenging free radicals in a mammal including a human, comprising administering a therapeutically effective amount of a chemical having the form

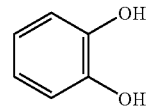

wherein the composition is formulated as a tablet, a capsule, a time release tablet, a time release capsule; a time release pellet; a sublingual tablet; a gel capsule; a microencapsulation; a transdermal delivery formulation; a transdermal gel; a transdermal patch; a sterile solution; a sterile solution prepared for use as an intramuscular or subcutaneous injection, for use as a direct injection into a targeted site, or for intravenous administration; a solution prepared for rectal administration; a solution prepared for administration through a gastric feeding tube or duodenal feeding tube; a suppository for rectal administration; a liquid for oral consumption prepared as a solution or an elixir; a topical cream; a gel; a lotion; a tincture; a syrup; an emulsion; or a suspension.
with that wherein said composition is formulated as a liquid for oral consumption prepared as a solution or an elixir, catechol is the only active ingredient.

In one embodiment of the present invention, the composition is further formulated for nutritional supplementation, dietary supplementation, food supplementation, nutraceutical administration or nutra-therapeutical administration; and formulated as a tablet, a capsule, a time release tablet, a time release capsule; a time release pellet, a sublingual tablet, a gel capsule, a microencapsulation, a liquid for oral consumption prepared as a solution or an elixir, a tincture, a syrup, an emulsion, or a suspension.

The invention encompasses methods for nutritional supplementation, dietary supplementation, food supplementation, nutraceutical administration or nutra-therapeutical administration in a subject including a human, comprising orally administering a composition set forth in the first, second, third, fourth, fifth, or sixth aspect of the invention; or a combination thereof.

In particular aspects of the invention, the compositions are directed to those comprising a salt of rhodizonic acid, an OH anion-generating base, a non-toxic acid, a quinone, a salt-containing sulfite, catechol, an antineoplast in the form of an acetogenin, an extract of green tea or one or more of the flavanoids contained in green tea or other similar plants such as catechin, epicatechin, epicatechin gallate, epigallocatechin, epigallocatechin gallate or other similar compounds such as flavone, myricetin, quercitin, or rutin. In a particular embodiment, the inventive composition consists essentially, or consists of, a salt of rhodizonic acid, an OH anion-generating base, a non-toxic acid, a quinone, a salt-containing sulfite, catechol, an antineoplast in the form of an acetogenin, an extract of green tea or one or more of the flavanoids contained in green tea or other similar plants such as catechin, epicatechin, epicatechin gallate, epigallocatechin, epigallocatechin gallate or other similar compounds such as flavone, myricetin, quercitin, or rutin.

The composition of the present invention provides significantly higher levels of antioxidants than the above-mentioned sources of vitamins E and C, broccoli, alpha-lipoic acid, and grapeseed, commonly accepted sources of antioxidants. The concentration of antioxidants of the present invention compared with these known sources is illustrated in FIG. 1 in which equivalent amounts of the natural sources are indicated compared with a single dose of the composition of the present invention.

Catechol, its Analogs and Equivalents

In contrast to previous determinations by NCI, FDA and ACS, the Applicant discovered that catechol possesses significant anti-cancer activity on a broad variety of cell lines when chronic cytotoxic dosing is achieved. Catechol also demonstrated significant antioxidant activity on all species of free radicals that it was tested upon. In fact, the Applicant unexpectedly found that catechol had the vast majority of anticancer and antioxidant properties in Cantron. Catechol is a biologically significant organic phenol. It comprises two hydroxyl groups attached to a benzene ring

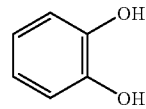

Catechol, its analogs and equivalents, as used herein may be characterized by the following:

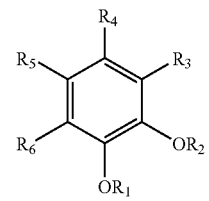

where $R_1$, $R_2$, $R_3$, $R_4$, $R_5$, $R_6$ may be any combination of hydrogen, alkyl, alkenyl hydroxyalkyl, carboxyl, aryl, alkenyl, cycloalkanes, cycloalkenes, glycine, glyco-saccharide, amino acid, peptide, polypeptide, protein and any of the foregoing attached to a central carbon, nitrogen, oxygen, sulfur, phosphorus or silicon atom. In addition, $R_1$, $R_2$, $R_3$, $R_4$, $R_5$, $R_6$ may be any of the R groups taken together will form a C3 to C10 membered ring.

As an antioxidant catechol may include flavone, flavonol, flavanone, isoflavone and anthocyane. Specifically, this may include flavone having the generic structure shown below (as a specific example luteolin is also illustrated):

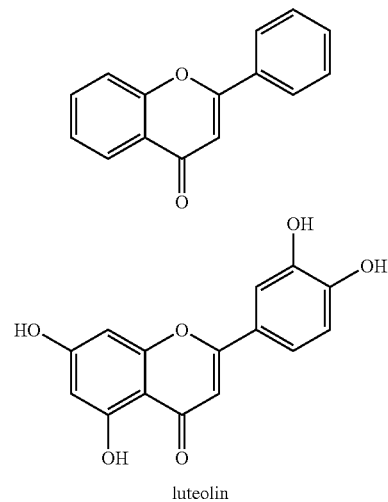

luteolin

As a flavonol it may have the generic structure shown below (as a specific example quercetin is also illustrated):

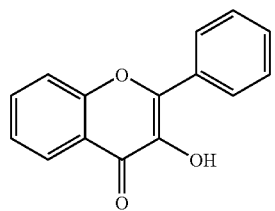

-continued

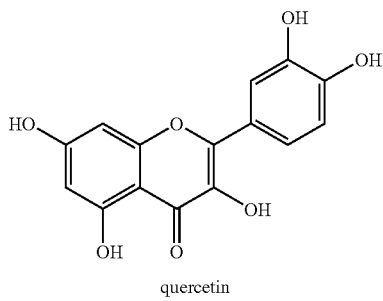
quercetin

As a flavanone it may have the generic structure shown below (as specific examples naringenin and taxifolin are also illustrated):

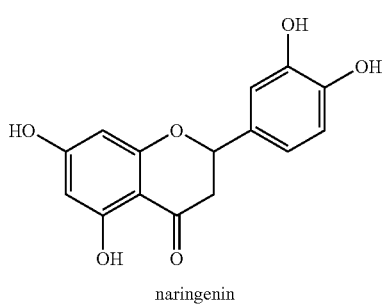
naringenin

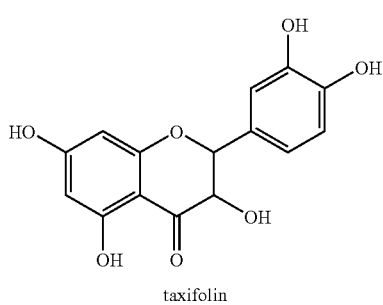
taxifolin

As an isoflavone it may have the generic structure shown below (as a specific example quercetin is also illustrated):

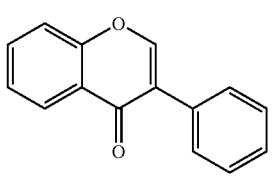

-continued

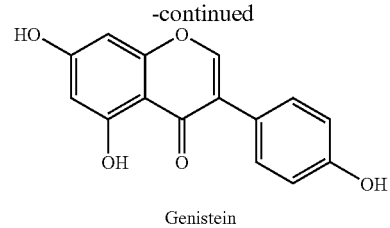
Genistein

Finally, as an anthocyane it may have the generic structure shown below (as a specific example cyanidin chloride is also illustrated)

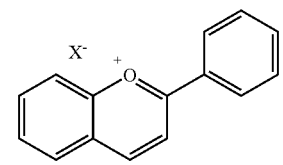

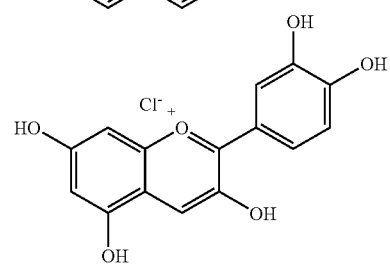
cyanidin chloride

Acetogenins

Acetogenins are active compounds which act as anti-neoplastic agents. They can be found as pure extracted compounds, including compounds such as asimicin or squamosin; crude extracts which contain about 10% pure compound; or they can be found in components of acetogenin containing botanicals including trees, plants or shrubs such as the Paw Paw or the Graviola tree. Components include bark, stems, leaves, twigs, branches or fruit.

It is known that acetogenins have powerful cytotoxicity on cancer cell lines, but the Applicant's clonogenic assays also uncovered the fact that acetogenin has highly selective anti-cancer activity. More importantly, however, the Applicant discovered that acetogenin worked in the same way as catechol. That is, the Applicant discovered that chronic cytotoxic dosing of tumor cells is required in order to achieve the desired efficacies; thereby necessitating inventive forms of administration to achieve optimum efficacy. Accordingly, the invention particularly encompasses time release and/or other chronic dosing administrative forms. It is believed that acetogenins act against cancer by regulating the production of ATP in the mitochondria of unhealthy cells. In some of its embodiments, the present invention combines the powerful and surprising synergistic effect of acetogenins with catechol. The addition of acetogenins in such embodiments improves the effectiveness of the catechol by destroying both resistant and non-resistant cells that otherwise might not be destroyed by catechol or acetogenin alone. This is important, as even a small number of cells left intact after treatment can multiply geometrically in little time, and can render either catechol or acetogenin useless. Further importantly, acetogenins kill multiple drug-resistant (MDR) cells which, in fact, may be resistant to catechol. The Applicant discovered surprising synergistic properties in the combination of catechol and acetogenin. The synergistic combination of these two compounds serves to block multiple pathways in the cancer cell and therefore yields greater cytotoxic effects than can be achieved by either component alone.

The compositions and formulations of the invention demonstrate positive effects against a broad variety of cancers, autoimmune and rheumatological diseases, including lupus and rheumatoid arthritis, and provide antioxidant protection against peroxyl radicals of both the hydrophillic and the lipophilic types, hydroxyl radicals, peroxynitrite radicals and super oxide radicals. The compositions and formulations of the invention also demonstrate positive effects against a broad variety of viruses such as Epstein Barre Virus and HIV. Accordingly, the compositions and formulations of the invention are useful for treating a broad variety of cancers, autoimmune-, rheumatological-, and virally mediated diseases, including those stated herein.

A First Preferred Composition

A preferred composition of the present invention includes the following essential ingredients. Other ingredients (for example, flavorings) may be added without deviating from the scope of the present invention. Thus, a first preferred composition of the invention comprises:

an antioxidant selected from the group consisting of a chemical having the form

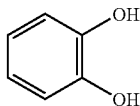

in the amount of between 1 g and 10,000 g (10 kg), preferably between 150 g and 900 g;
an anti-neoplastic agent selected from the group consisting of acetogenin, its analogs and its equivalents in the amount of between 1 mg and 2,000 g (2 kg) and preferably between 3 grams and 30 grams of pure acetogenin compound;
an acid selected from the group consisting of croconic acid, its analogs and its equivalents and sulfites of croconic acid, their analogs and their equivalents in the amount of between 1 g and 1500 g (1.5 kg) and preferably between 10 g and 30 g; and
a quinone selected from the group consisting of tetrahydroxyquinone, its analogs and its equivalents and/or sulfites of tetrahydroxyquinone, their analogs and their equivalents in the amount of between 1 g and 2,500 g (2.5 kg), preferably between 10 g and 40 g.

A Second Preferred Composition

A particular embodiment of the first preferred composition is herein described as the second preferred composition. That is, to increase the anticancer activity and the antioxidant effects of the first preferred composition on 4 of the 5 types of free radicals and to prevent croconic acid's unexpected inhibition of the composition's antioxidant activity upon peroxynitrite and superoxide radicals, croconic acid and sulfites of croconic acid can be replaced by an extract of green tea or by flavanoids that have similar antioxidant properties. The suitable flavanoids for the purposes of the present invention include catechin, epicatechin, epicatechin gallate, epigallocatechin, epigallocatechin gallate, quercitin, rutin, flavone and myricetin. In addition to the significant additive effects upon peroxyl, peroxynitrite and superoxide radicals, the addition of green tea extract yields a powerful and unexpected synergistic effect upon hydroxyl and peroxyl (hydrophilic) radicals. Green tea extract, when combined with catechol, also yields powerful synergistic anticancer effects on a broad variety of cancers (catechol and acetogenin also have powerful synergistic properties). Free form THQ and acetogenin further compounds the synergistic anticancer effect of the composition. The second preferred composition utilizes free form THQ instead of sulfited THQ.

General Method for Making the First Preferred Composition Described Above

The composition of the present invention may be prepared by the following general procedures:

Step 1:

Create a suspension of a salt of rhodozonic acid ($C_6O_6Na_2$) and any base that can generate OH anions by mixing both in a flask with water. (It should be noted that analogs and equivalents of rhodozonic acid could be substituted for rhodozonic acid.) The amount of the water is preferably between 1 mL and 10,000 mL (10 L) and more preferably between 300 mL and 1000 mL (1 L). The amount of the rhodozonic acid is preferably between 1 g and 7300 g (7.3 kg) and is more preferably between 100 g in 150 g. The base is taken from the group consisting of KOH, LiOH, NaOH, Mg(OH)$_2$, and Ca(OH)$_2$. The amount of base is preferably between 1 g and 500 g and is more preferably between 100 g and 200 g Step 2:

Heat the suspension created in Step 1 to reflux until all of the rhodizonic acid is dissolved and the solution becomes bright yellow. The yellow color is indicative of the formation of croconic acid dipotassium salt ($C_5O_5K_2$, yield=20% by HPLC, 0.116 moles). Preferably the suspension is heated to between 25° C. and 100° C. More preferably the suspension is heated to between 90° C. and 100° C. The step of dissolving the rhodizonic acid takes about two hours. The new suspension demonstrates a pH of about 13.0.

Alternative Initial Step (Alternative to Steps 1 and 2):

Create a solution by adding between 1 g and 1500 g (1.5 kg) and preferably between 15 g and 30 g of croconic acid ($C_5O_5K_2$) to between 1 mL and 10,000 mL of water and more preferably to between 300 mL and 1000 mL of water to form a solution. (It should be noted that analogs and equivalents of croconic acid could be substituted for croconic acid.)

Step 3:

Bring the pH of the solution formed in Step 2 (or the solution formed in the Alternative Initial Step) to between preferably 7.0 and 10.0 and more preferably between 9.0 and 9.4.

Step 4:

Add tetrahydroxy-1,4-quinone ($C_6H_4O_6$) to the solution of Step 3, resulting in a black suspension. The tetrahydroxy-1,4-quinone is provided preferably in an amount of between 1 g and 2500 g (2.5 kg) and more preferably in an amount of between 40 g and 80 g. (Analogs and equivalents of tetrahydroxy-1,4-quinone may be substituted for tetrahydroxy-1,4-quinone.)

Step 5:

Add water and heat the suspension of Step 4 to completely dissolve all materials. Preferably between 1 mL and 2000 mL of water is used, and more preferably between 1000 mL and 1500 mL of water is used. Heating is preferably between 70° C. and 100° C. and is more preferably between 85° C. and 100° C. Dissolution of the materials preferably occurs between 1 and 180 minutes and more preferably occurs between 5 minutes and 60 minutes.

Step 6:

Dissolve a salt containing a sulfite ($SO_3^{-2}$) in water and add to the flask of the solution of Step 5. The salt used in Step 6 is preferably taken from the group consisting of Na$_2$SO$_3$, $Li_2SO_3$, $K_2SO_3$, $MgSO_3$, and $Ca_2SO_3$. The amount of sulfite used in this step is preferably between 1 g and 10,000 g (10 kg) and is more preferably between 1000 g (1 kg) and 3000 g (3 kg). The amount of water used in this step is preferably between 1 mL and 20,000 mL and more preferably is in the range of between 5000 mL and 7000 mL.

As an alternative to the addition of a salt containing a sulfite a sulfurous acid may be added to the base to generate sodium sulfite in situ.

Step 7:

Adjust the pH of the solution formed in Step 6 to preferably between 5.0 and 7.9 and more preferably to between 6.5 and 6.9.

Step 8:

Heat the mixture of Step 7 first to preferably between 60° C. and 100° C. and more preferably between 90° C. and 100° C. for preferably between 1 minute and 60 minutes and more preferably between 5 and 10 minutes.

Step 9:

Heat the mixture of Step 8 first to preferably between 0° C. and 100° C. and more preferably between 85° C. and 95° C. for preferably between 1 minute and 180 minutes and more preferably between 45 and 60 minutes. A black precipitate solution will form.

Step 10:

Allow the solution of Step 9 to cool to preferably between 0° C. and 60° C. and more preferably to between 20-25° C.

Step 11:

Dissolve between 1 g and 10,000 g (10 kg) and preferably between 150 g and 750 g of catechol ($C_6H_6O_2$) in water and add to the solution of Step 10. The amount of water used in this step is preferably between 1 mL and 5000 mL and more preferably is in the range of between 1000 mL and 2000 ml. (Analogs and equivalents of catechol may be substituted for catechol).

Step 12:

Adjust the pH of the suspension of Step 11 to preferably between 1.0 and 12.0 and more preferably to between 7.0 and 7.5.

Step 13:

An acetogenin (including its analogs and equivalents) may be added to the composition of Step 12 preferably in the amount of between 0.1 mg to 2000 g (2 kg) and, more preferably, in the amount of between 3 g and 30 g. The addition of an acetogenin will synergistically enhance the cancerous cell-killing potency of the composition, and particularly on drug-resistant (MDR) cells.

Step 14:

Increase the final volume of the solution of Step 12 (or optionally Step 13) by adding water preferably in the amount of between 5 L and 100 L and more preferably in the amount of between 10 L and 15 L Step 15:

Lyophilize (freeze-dry), vacuum dry or spray dry the liquid to create a dry powder or granules.

Additional Steps (Optional):

The dry powder or granules can be added to other preparations including but not limited to foods and pet foods; or utilized in other preparations such as a time release tablet, a time release capsule, time release pellets or where the time release pellets are added to other preparations including but not limited to foods and pet foods; tablets or capsules of the non-time release variety including sublingual tablets; gel capsules; microencapsulation; topical creams, gels or lotions; transdermal delivery including a transdermal gel or transdermal patch; a sterile solutions prepared for use as an intramuscular or subcutaneous injection, a direct injection into a targeted site, or for intravenous administration; a solution prepared for rectal administration, or for administration through a gastric feeding tube or duodenal feeding tube; a suppository for rectal administration; coupled with or administered with known delivery systems including inert carriers or attached to a polymer to form a drug carrier designed to reach targeted sites. The dry powder or granules can also be used to prepare administrative forms selected from a group consisting of an oral liquid; and elixir, a tincture, a syrup, an emulsion, or a suspension.

General Method for Making the Second Preferred Composition

Catechol ($C_6H_6O_2$) in the amount of between 1 g and 10,000 g (10 kg) and more preferably in the amount of between 300 g and 900 g is combined with an acetogenin preferably in the amount of between 0.1 mg and 2000 g (2 kg) and more preferably in the amount of between 3 g and 50 g of pure compound or between 30 g and 500 g of plant extracts containing 10% acetogenins. There are over 1000 different types of this compound such as asimicin or squamosin plus extracts from source plants such as Paw Paw or Graviola. Tetrahydroxy-1,4-quinone ($C_6H_4O_6$) is then added, preferably in the amount between 1 g to 2500 g (2.5 kg) and more preferably between 10 g and 40 g. Finally between 2 grams and 20,000 grams and preferably between 600 g and 1200 g of an extract of green tea or flavanoids that have similar antioxidant properties such as catechin, epicatechin, epicatechin gallate, epigallocatechin, epigallocatechin gallate, quercitin, rutin, flavone and myricetin is added.

Additional Steps (Optional):

This powder can then be added to other preparations including but not limited to foods and pet foods; or utilized in other preparations such as a time release tablet, a time release capsule, time release pellets or where the time release pellets are added to other preparations including but not limited to foods and pet foods; tablets or capsules of the non-time release variety including sublingual tablets; gel capsules; microencapsulation; topical creams, gels or lotions; transdermal delivery including a transdermal gel or transdermal patch; a sterile solutions prepared for use as an intramuscular or subcutaneous injection, a direct injection into a targeted site, or for intravenous administration; a solution prepared for rectal administration, or for administration through a gastric feeding tube or duodenal feeding tube; a suppository for rectal administration; coupled with or administered with known delivery systems including inert carriers or attached to a polymer to form a drug carrier designed to reach targeted sites. The powder can also be used to prepare administrative forms selected from a group consisting of an oral liquid; an elixir, a tincture, a syrup, an emulsion, or a suspension.

Additional Component—Time Release Mechanism

In vitro studies have verified that the above-mentioned Cantron® has anti-cancer activity. However, the Applicant discovered that chronic dosing is required in order for this composition to be effective. This axiom holds true for the known composition, for its main active ingredient catechol when used as an individual ingredient composition or in a multi-ingredient composition or for acetogenin when used as an individual ingredient composition or in a multi-ingredient composition.

The half-life of the Cantron® formula was thought, at one time, to be between six and eight hours. Importantly, recent studies undertaken by the inventor of the present composition and its method of formulation have shown, surprisingly, that catechol, the biomarker for Cantron®, only stays in the bloodstream for a maximum of two hours and only stays in tumors for one hour.

According to the present invention, the delivery system has been altered by providing a time release formulation to obtain optimum anti-cancer effects by delivering a constant supply of the active ingredients into the bloodstream. It is this chronic exposure to tumors which obtains full efficacy of the present composition. This approach also delivers a constant supply of antioxidants into the bloodstream thereby providing superior protection against free radical damage to blood, blood vessels, tissues, proteins and cellular structures and thereby creates a greater prophylactic treatment for over 50 disease states that are engendered by free radical damage.

To affect a time release mechanism in the various compositions of the present invention, once the liquid material is produced as set forth above, the liquid is converted to a dry powder form by techniques such as lypholization, freeze-drying, spray-drying, or vacuum drying. The powder is then coated to produce time release beads or pellets. Capsules (gelatin or non-gelatin) are then filled with the beads or pellets. The time release beads may be used in food, in animal food, or in animal treats. Alternatively, the powder can be converted to time release tablets.

The time release formulation provides significant advantages over the prior art by sustaining an effective amount of the composition in the user's bloodstream and/or tumor sites at all times while medicated. Effectiveness of the time release formulation of the present composition is addressed below with respect to FIG. 2.

To create a time release pill, the dried powder from step 15 is utilized. The optimum method to manufacture the time release composition is a controlled release tablet, capsule, or pellets which dissolves continuously over 12 hours.

To create time release pellets or capsules, Hydroxypropyl Methylcellulose and Shellac can be used as polymers along with organic sucrose and silicon dioxide as flow agents and absorbents, and talc as a lubricant and filler. Other polymers, flow agents, absorbents, lubricants and fillers that are commonly known in the industry can be substituted accordingly.

Type: Controlled Release—dissolves continuously over 12 hours

The dissolution broad specification for the time release pellets and capsules is:
   1 hour 10-40%
   4 hours 35-75%
   8 hours 70-95%
   12 hours not less than 85%

For freeze-dried Cantron® (New Millennium version used) in time-release capsule form, the actual measurement is:
   1 Hour 35.75%
   4 Hours 73.85%
   8 Hours 91.27%
   12 Hours 98.63%

To create a time release tablet Methocel K15 and Ethocel can be utilized as polymers along with microcrystalline cellulose as an excipient and binder, silicon dioxide as a flow agent and absorbent, and magnesium stearate as filler and lubricant. Other polymers, flow agents, absorbents, lubricants and fillers that are commonly known in the industry can be substituted accordingly.

Type: Slow Release—Dissolves Continuously Over 12 Hours

Dissolution Broad Specification:
   1 Hour: 10%-40%
   4 Hours: 35%-75%
   8 Hours: 70%-95%
   12 Hour: Not less than 85%

For the composition: catechol (34.5%), THQ (8.9%), green tea extract (56.6%) in time release tablet form (weight to weight), the actual measurement is:
   1 Hour 39%
   4 Hours 72.5%
   8 Hours 80%
   12 Hours 90.4%

Administration of the Composition

Regardless of the selected composition, the formulation of the present invention may be administered in any one of a variety of methods. A combination of these methods may also be used. These methods include liquid, powder or gel forms. The composition may be administered externally by transdermal delivery, which includes a transdermal gel and a transdermal patch. The formula could be attached to a polymer to create a targeted drug to reach tumor sites. Regardless of the form of the composition, the objective is to achieve and maintain an effective amount of the composition in the patient's bloodstream and at the tumor site. All of the new forms of delivery discussed hereafter eliminate the negative appeal of the dark black liquid of earlier compositions while improving dosage compliance, optimum efficiency, and eliminate the staining of teeth and clothing that was an inherent characteristic of these earlier compositions.

Intravenous, Intramuscular, Intraperitoneal, Subcutaneous or Rectal Administration When administered in liquid form, the composition may be introduced via intravenous delivery. Intravenous administration particularly assures that an effective amount of the composition can be maintained in the patient's bloodstream at all times. As a further variant of the intravenous form of administration the composition of the present invention may be injected directly into the patient. A solution or suppository for rectal administration also can be utilized.

Oral Administration

When administered in liquid form, the composition may also be introduced orally. An optional approach for oral administration for the liquid composition is administrative by way of a gel capsule. To manufacture a gel capsule, the dried powder from step is added to a capsule containing gelatin, glycerin, and sorbitol or other methods known to one skilled in the arts, As set forth above, an alternative to the liquid form of the composition is to convert the liquid composition form to a dry powder form, when necessary. The dry powder may then be tabletized and conveniently administered as a tablet (including sublinqual tablets) or may be coated with an enteric coating, or a time release agent then encapsulated as discussed above.

Non-time release oral forms of the composition of the present invention as described above should be taken every two hours during waking hours in either one or two tablets or capsules. The patient is given a double dose before retiring for the night. No more than six hours should elapse between doses.

Powder, granules or time release pellets may be added to foods, animal foods or animal treats.

External Administration

As an alternative to the intravenous and oral techniques for administering the composition of the present invention, the composition may be delivered transdermally by use of a patch or a transdermal gel. If administered as a patch, a single patch is attached to the patient's pulse point and is replaced every four to twelve hours. In either event, the transdermal delivery mechanism provides a constant supply of the active ingredients of the present invention to the patient's bloodstream. The formulations can also be administered in a cream, a lotion, or a gel.

Targeted Drug Carriers

The formula can be attached to an inert carrier or to a polymer to reach targeted sites such as tumors.

The following examples include non-limiting examples methods of producing the compositions of the present invention.

EXAMPLE 1

Method of Making the First Preferred Composition

A suspension of rhodizonic acid disodium salt ($C_6O_6Na_2$, 124 g, 0.58 moles) and KOH (2N, 168 g 1, 0.5 L, pH=12.4) was created by mixing the two components together in a 10 L flask. This suspension was heated for approximately two hours to reflux until all of the rhodizonic acid disodium salt was dissolved and the solution became bright yellow. HCL (2N, 200 ml) was then added to the solution to bring the pH of the solution formed to 9.2. (It should be noted that while an acid was added to the solution to adjust the pH to its desired level, it may be required in the alternative to use a base to make the same adjustment in a different experiment.) Tetrahydroxy-1,4-quinone ($C_6H_4O_6$, 50.4 g, 7.1 moles) was added to the solution to achieve a black suspension. Water was next added (1.3 L). The suspension was heated to 90° C. for 10 minutes to completely dissolve all of the materials. Sodium sulfite ($Na_2SO_3$, 1490 g, 11.8 moles) was dissolved in 6 L of water and was added to the 10 L flask of the solution. HCl was then added to bring the pH of the solution to 6.5-6.9.

The resulting mixture was heated first to 100° C. for 10 minutes and was then heated again to 90° C. for 50 minutes, resulting in the formation of a black precipitate solution. This solution was allowed to cool to room temperature (20-25° C.). An amount of Catechol ($C_6H_6O_2$, 365 g, 3.12 moles) was dissolved in 2 L of water. This was added to the solution. The pH of this suspension was adjusted to between 7.0-7.5. The final volume of the solution thus achieved was increased to 13 L by adding water, or alternatively to adding water, the solution was lyophilized, vacuum dried or spray dried to create a dry powder, which is then suitable to be used in multiple preparations. Optionally, an acetogenin (including its analogs and equivalents) may be added to the dry powder preferably in the amount of between 0.1 mg to 2000 g (2 kg) and, more preferably, in the amount of between 3 g and 50 g of pure compound or between 30 g and 500 g of a plant extract containing approximately 10% acetogenins. The resultant dry powder can be utilized in its pure form or formulated into a tablet, a capsule, a time release tablet or capsule or time release pellets, preferably of the controlled release nature utilizing shellac, and hydroxypropyl methylcellulose as polymers for the time release pellets or capsules and Methocell 15 and Ethocel as polymers for the time release tablets. The dry powder can also be added to foods and pet foods, to a preparation for the manufacture of a transdermal gel or transdermal patch, to a preparation for the manufacture of a topical cream or ointment, to a mixture of gelatin, glycerin and sorbitol to create a gel capsule, to a sterilized solution to create an intravenous preparation, to a sterilized vial for direct injection, or to a mechanical device with pump and syringe for rectal administration. The time release pellets can be added to foods or pet foods.

EXAMPLE 2

Method of Making the Second Preferred Composition

Step 1: Catechol ($C_6H_6O_2$) in the amount of between 1 g and 10,000 g (10 kg) and more preferably in the amount of between 300 g and 900 g is combined with an acetogenin preferably in the amount of between 0.1 mg and 2000 g (2 kg) and more preferably in the amount of between 3 g and 50 g of pure compound or between 30 g and 500 g of plant extracts containing 10% acetogenins. There are over 1000 different types of this compound such as asimicin or squamosin plus extracts from source plants such as Paw Paw or Graviola.

Step 2: Free form Tetrahydroxy-1,4-quinone ($C_6H_4O_6$) is then added, preferably in the amount between 1 g to 2500 g (2.5 kg) and more preferably between 10 g and 80 g.

Step 3: Between 2 grams and 20,000 grams and preferably between 600 g and 1200 g of an extract of green tea or flavanoids that have similar antioxidant properties such as catechin, epicatechin, epicatechin gallate, epigallocatechin, epigallocatechin gallate, quercitin, rutin, flavone and myricetin is added.

The powder can then be formulated into any one of the inventive administrative forms which have already described herein.

EXAMPLE 3

Variants of the First and Second Preferred Compositions

While the first and second compositions have been set forth above, a number of variations of these compositions have demonstrated characteristics that are similar to those of the first and second compositions. These variants were prepared according to the following.

I. Variants with Catechol

IA. Catechol Plus Acetogenins

Catechol ($C_6H_6O_2$) in the amount of between 1 g and 10,000 g (10 kg) and more preferably in the amount of between 150 g and 750 g is combined with an acetogenin preferably in the amount of between 0.1 mg and 2000 g (2 kg) and more preferably in the amount of between 80 g and 100 g. There are over 1000 different types of this compound plus extracts from source plants. The powder can then be formulated into any one of the inventive administrative forms which have already been described herein.

IB. Catechol Plus THQ

Tetrahydroxy-1,4-quinone ($C_6H_4O_6$) preferably in the amount of between 1 g to 2500 g (2.5 kg) and more preferably between 40 g and 80 g is combined with catechol ($C_6H_6O_2$) preferably in the amount of between 1 g and 10,000 g (10 kg) and more preferably in the amount of between 150 g and 750 g. The powder can then be formulated into any one of the inventive administrative forms which have already been described herein.

IC. Catechol Plus THQ Sulfite

Step 1:

Tetrahydroxy-1,4-quinone ($C_6H_4O_6$) preferably in the amount of between 1 g to 2500 g (2.5 kg) and more preferably between 40 g and 80 g is suspended in 3 liters of water and heated at 90° C. for 10 minutes to completely dissolve all materials.

Step 2:

Dissolve a sulfite-containing salt preferably in the amount of between 1 g and 10,000 g (10 kg) and more preferably in the amount of between 1000 kg (1 kg) and 3000 g (3 kg) in 6 L of water and add to the solution created in Step 1.

Step 3:

Adjust the pH of the solution of Step 2 to 6.5-6.9.

Step 4:

Heat the mixture of Step 3 first (at sub-step (a)) to 100° C. for 10 minutes followed second by heating (at sub-step (b)) to 90° C. for 50 minutes.

Step 5:

Catechol (in ranges along the lines set forth above with respect to the preferred embodiment of the present invention) is added and the mixture is stirred to dissolve the catechol. This mixture was freeze dried to a powder. The powder can then be formulated into any one of the inventive administrative forms which have already been described herein.

ID. Catechol Plus Croconic Acid

Step 1:

Create a suspension of a salt of rhodozonic acid and any base that can generate OH anions by mixing both in a 10 L flask with water. The amount of the water is preferably between 1 mL and 10,000 mL (10 L) and more preferably between 300 mL in 1000 mL (1 L). The amount of the rhodozonic acid is preferably between 1 g and 7300 g (7.3 kg) and is more preferably between 100 g in 150 g. The base is taken from the group consisting of KOH, LiOH, NaOH, Mg $(OH)_2$, and Ca $(OH)_2$. The amount of base is preferably between 1 g and 500 g and is more preferably between 100 g and 200 g.

Step 2:

Heat the suspension created in Step 1 to reflux until all rhodizonic acid disodium salt is dissolved and the solution becomes bright yellow, approximately 2 hours. The yellow color is indicative of the formation of croconic acid dipotassium salt ($C_5O_5K_2$, yield=20% by HPLC).

Alternative Initial Step (Alternative to Steps 1 and 2):

Create a solution by adding between 1 g and 1500 g (1.5 kg) and preferably between 15 g and 30 g of croconic acid ($C_5O_5K_2$) to between 1 mL and 10,000 mL of water and more preferably to between 300 mL and 1000 mL of water to form a solution. (It should be noted that analogs and equivalents of croconic acid could be substituted for croconic acid.)

Step 3:

Adjust the pH of the solution formed in Step 2 to 7.4 (6.9-7.9).

Step 4:

Catechol (in ranges along the lines set forth above with respect to the preferred embodiment of the present invention) was added and the mixture is stirred to dissolve catechol. This mixture was freeze dried to a powder. The powder can then be formulated into any one of the inventive administrative forms which have already been described herein.

IE. Catechol Plus Croconic Acid Sulfite

Step 1:

Create a suspension of a salt of rhodozonic acid and any base that can generate OH anions by mixing both in a 10 L flask with water. The amount of the water is preferably between 1 mL and 10,000 mL (10 L) and more preferably between 300 mL in 1000 mL (1 L). The amount of the rhodozonic acid is preferably between 1 g and 7300 g (7.3 kg) and is more preferably between 100 g in 150 g. The base is taken from the group consisting of KOH, LiOH, NaOH, Mg $(OH)_2$, and Ca $(OH)_2$. The amount of base is preferably between 1 g and 500 g and is more preferably between 100 g and 200 g.

Step 2:

Heat the suspension created in Step 1 to reflux until all rhodizonic acid disodium salt is dissolved and the solution becomes bright yellow, approximately 2 hours. The yellow color is indicative of the formation of croconic acid dipotassium salt ($C_5O_5K_2$, yield=20% by HPLC). (Note that as an alternative to forming croconic acid in the suspension croconic acid may be added directly. If this option is selected, preferably between 1 g and 1500 g (1.5 kg) and more preferably between 15 g and 30 g of croconic acid may be added preferably to between 1 mL and 10,000 mL of water and more preferably to between 300 mL and 1000 mL of water to form a solution.)

Alternative Initial Step (Alternative to Steps 1 and 2):

Create a solution by adding between 1 g and 1500 g (1.5 kg) and preferably between 15 g and 30 g of croconic acid ($C_5O_5K_2$) to between 1 mL and 10,000 mL of water and more preferably to between 300 mL and 1000 mL of water to form a solution. (It should be noted that analogs and equivalents of croconic acid could be substituted for croconic acid.)

Step 3:

Adjust the pH of the solution formed in Step 2 to 9.2 (9.0-9.4).

Step 4:

Dissolve a sulfite-containing salt preferably in the amount of between 1 g and 10,000 g (10 kg) and more preferably in the amount of between 1000 kg (1 kg) and 3000 g (3 kg) in 6 L of water and add to the solution created in Step 3.

Step 5:

Adjust the pH of the solution of Step 4 to 6.5-6.9.

Step 6:

Heat the mixture of Step 5 first (at sub-step (a)) to 100° C. for 10 minutes followed second by heating (at sub-step (b)) to 90° C. for 50 minutes.

Step 7:

Catechol (in ranges along the lines set forth above with respect to the preferred embodiment of the present invention) was added and the mixture was stirred to dissolve catechol. This mixture was freeze dried to a powder. The powder can then be formulated into any one of the inventive administrative forms which have already been described herein.

IF. Catechol, Plus THQ and an Extract of Green Tea

Tetrahydroxy-1,4-quinone ($C_6H_4O_6$) preferably in the amount of between 1 g to 2500 g (2.5 kg) and more preferably between 10 g and 80 g is combined with catechol ($C_6H_6O_2$) preferably in the amount of between 1 g and 10,000 g (10 kg) and more preferably in the amount of between 300 g and 900 g. An extract of green tea or flavanoids that have similar antioxidant properties such as catechin, epicatechin, epicatechin gallate, epigallocatechin, epigallocatechin gallate, quercitin, rutin, flavone and myricetin is then added preferably in the amount between 2 grams and 20,000 grams and more preferably between 600 g and 1200 g. The powder can then be formulated into any one of the inventive administrative forms which have already been described herein.

IG. Catechol Plus an Extract of Green Tea

Catechol ($C_6H_6O_2$) preferably in the amount of between 1 g and 10,000 g (10 kg) and more preferably in the amount of between 300 g and 900 g is added to an extract of green tea or flavanoids that have similar antioxidant properties such as catechin, epicatechin, epicatechin gallate, epigallocatechin, epigallocatechin gallate, quercitin, rutin, flavone and myricetin, preferably in the amount between 2 grams and 20,000 grams and more preferably between 600 g and 1200 g. The powder can then be formulated into any one of the inventive administrative forms which have already been outlined in the general method for making the preferred composition.

Ii. Variants with Acetogenins

IIA. Acetogenin Plus THQ

Tetrahydroxy-1,4-quinone ($C_6H_4O_6$) preferably in the amount of between 1 g to 2500 g (2.5 kg) and more preferably between 40 g and 80 g is mixed with an acetogenin preferably in the amount of between 0.1 mg and 2000 g (2 kg) and more preferably in the amount of between 80 g and 100 g. The components were mixed as solids. The powder can then be formulated into any one of the inventive administrative forms which have already been described herein.

IIB. Acetogenin Plus THQ Sulfite

Step 1:
Tetrahydroxy-1,4-quinone ($C_6H_4O_6$) preferably in the amount of between 1 g to 2500 g (2.5 kg) and more preferably between 40 g and 80 g is suspended in 3 liters of water and heated at 90° C. for 10 minutes to completely dissolve all materials.

Step 2:
Dissolve a sulfite-containing salt preferably in the amount of between 1 g and 10,000 g (10 kg) and more preferably in the amount of between 1000 kg (1 kg) and 3000 g (3 kg) in 6 L of water and add to the solution created in Step 1.

Step 3:
Adjust the pH of the solution of Step 2 to 6.5-6.9.

Step 4:
Heat the mixture of Step 3 first (at sub-step (a)) to 100° C. for 10 minutes followed second by heating (at sub-step (b)) to 90° C. for 50 minutes.

Step 5:
This solution is freeze dried to a powder.

Step 6:
An acetogenin, preferably in the amount of between 0.1 mg and 2000 g (2 kg) and more preferably in the amount of between 80 g and 100 g, is added to the powder in Step 5. The materials are then blended. This blended material is made into a powder. The powder can then be formulated into any one of the inventive administrative forms which have already been described herein.

IIC. Acetogenin Plus Croconic Acid

Step 1:
Create a suspension of a salt of rhodozonic acid and any base that can generate OH anions by mixing both in a 10 L flask with water. The amount of the water is preferably between 1 mL and 10,000 mL (10 L) and more preferably between 300 mL in 1000 mL (1 L). The amount of the rhodozonic acid is preferably between 1 g and 7300 g (7.3 kg) and is more preferably between 100 g in 150 g. The base is taken from the group consisting of KOH, LiOH, NaOH, Mg $(OH)_2$, and Ca $(OH)_2$. The amount of base is preferably between 1 g and 500 g and is more preferably between 100 g and 200 g.

Step 2:
Heat the suspension created in Step 1 to reflux until all rhodizonic acid disodium salt is dissolved and the solution becomes bright yellow, approximately 2 hours. The yellow color is indicative of the formation of croconic acid dipotassium salt ($C_5O_5K_2$, yield=20% by HPLC).

Alternative Initial Step (Alternative to Steps 1 and 2):
Create a solution by adding between 1 g and 1500 g (1.5 kg) and preferably between 15 g and 30 g of croconic acid ($C_5O_5K_2$) to between 1 mL and 10,000 mL of water and more preferably to between 300 mL and 1000 mL of water to form a solution. (It should be noted that analogs and equivalents of croconic acid could be substituted for croconic acid.)

Step 3:
Adjust the pH of the solution formed in Step 2 to 7.4 (6.9-7.9)

Step 4:
This solution is freeze dried to a powder.

Step 5:
An acetogenin in the amount of between 0.1 mg and 2000 g (2 kg) and more preferably in the amount of between 80 g and 100 g is added to the powder from Step 4. The powder can then be formulated into any one of the inventive administrative forms which have already been described herein.

IID. Acetogenin Plus Croconic Acid Sulfite

Step 1:
Create a suspension of a salt of rhodozonic acid and any base that can generate OH anions by mixing both in a 10 L flask with water. The amount of the water is preferably between 1 mL and 10,000 mL (10 L) and more preferably between 300 mL in 1000 mL (1 L). The amount of the rhodozonic acid is preferably between 1 g and 7300 g (7.3 kg) and is more preferably between 100 g in 150 g. The base is taken from the group consisting of KOH, LiOH, NaOH, Mg $(OH)_2$, and Ca $(OH)_2$. The amount of base is preferably between 1 g and 500 g and is more preferably between 100 g and 200 g.

Step 2:
Heat the suspension created in Step 1 to reflux until all rhodizonic acid disodium salt is dissolved and the solution becomes bright yellow, approximately 2 hours. The yellow color is indicative of the formation of croconic acid dipotassium salt ($C_5O_5K_2$, yield=20% by HPLC).

Alternative Initial Step (Alternative to Steps 1 and 2):
Create a solution by adding between 1 g and 1500 g (1.5 kg) and preferably between 15 g and 30 g of croconic acid ($C_5O_5K_2$) to between 1 mL and 10,000 mL of water and more preferably to between 300 mL and 1000 mL of water to form a solution. (It should be noted that analogs and equivalents of croconic acid could be substituted for croconic acid.)

Step 3:
Adjust the pH of the solution formed in Step 2 to 9.0-9.4.

Step 4:
Dissolve a sulfite-containing salt preferably in the amount of between 1 g and 10,000 g (10 kg) and more preferably in the amount of between 1000 kg (1 kg) and 3000 g (3 kg) in 6 L of water and add to the solution created in Step 3.

Step 5:
Adjust the pH of the solution of Step 4 to 6.5-6.9.

Step 6:
Heat the mixture of Step 5 first (at sub-step (a)) to 100° C. for 10 minutes followed second by heating (at sub-step (b)) to 90° C. for 50 minutes.

Step 7:
The solution is freeze dried to a powder.

Step 8:
An acetogenin preferably in the amount of between 0.1 mg and 2000 g (2 kg) and more preferably in the amount of between 80 g and 100 g is added to the powder from Step 7. The powder can then be formulated into any one of the inventive administrative forms which have already been described herein.

IIE. Acetogenin Plus an Extract of Green Tea

An extract of green tea or one or more flavanoids that have similar antioxidant properties such as catechin, epicatechin, epicatechin gallate, epigallocatechin, epigallocatechin gallate, quercitin, rutin, flavone and myricetin, preferably in the amount between 2 grams and 20,000 grams and more preferably between 600 g and 1200 g is mixed with an acetogenin preferably in the amount of between 0.1 mg and 2000 g (2 kg) and more preferably in the amount of between 3 g and 50 g of pure compound or between 30 g and 500 g of an acetogenin plant extract containing 10% acetogenins. The powder can then be formulated into any one of the inventive administrative forms which have already been described herein.

IIF. Acetogenin Plus an Extract of Green Tea and THQ

Tetrahydroxy-1,4-quinone ($C_6H_4O_6$) preferably in the amount of between 1 g to 2500 g (2.5 kg) and more preferably between 10 g and 80 g is mixed with an acetogenin preferably in the amount of between 0.1 mg and 2000 g (2 kg) and more preferably in the amount of between 3 g and 50 g of pure compound or between 30 g and 500 g of an acetogenin plant extract containing 10% acetogenins and an extract of green tea or one or more flavanoids that have similar antioxidant properties such as catechin, epicatechin, epicatechin gallate, epigallocatechin, epigallocatechin gallate, quercitin, rutin, flavone and myricetin, preferably in the amount between 2 grams and 20,000 grams and more preferably between 600 g and 1200 g. The powder can then be formulated into any one of the inventive administrative forms which have already been described herein.

III. Variants with THQ

IIIA. THQ Sulfite Plus Croconic Acid Sulfite

Step 1:

Create a suspension of a salt of rhodozonic acid and any base that can generate OH anions by mixing both in a 10 L flask with water. The amount of the water is preferably between 1 mL and 10,000 mL (10 L) and more preferably between 300 mL and 1000 mL (1 L). The amount of the rhodozonic acid is preferably between 1 g and 7300 g (7.3 kg) and is more preferably between 100 g and 150 g. The base is taken from the group consisting of KOH, LiOH, NaOH, Mg (OH)$_2$, and Ca (OH)$_2$. The amount of base is preferably between 1 g and 500 g and is more preferably between 100 g and 200 g.

Step 2:

Heat the suspension created in Step 1 to reflux until all rhodizonic acid disodium salt is dissolved and the solution becomes bright yellow, approximately 2 hours. The yellow color is indicative of the formation of croconic acid dipotassium salt ($C_5O_5K_2$, yield=20% by HPLC).

Step 3:

Adjust the pH of the solution formed in Step 2 to 9.0-9.4.

Step 4:

Tetrahydroxy-1,4-quinone ($C_6H_4O_6$) preferably in the amount of between 1 g to 2500 g (2.5 kg) and more preferably between 40 g and 80 g is suspended in the solution of Step 3, resulting in a black suspension.

Step 5:

Add water (1.3 L) and heat the suspension of Step 4 to 90° C. for 10 minutes to completely dissolve all materials.

Step 6:

Dissolve a sulfite-containing salt preferably in the amount of between 1 g and 10,000 g (10 kg) and more preferably in the amount of between 1000 kg (1 kg) and 3000 g (3 kg) in 6 L of water and add to the solution created in Step 5.

Step 7:

Adjust the pH of the solution of Step 6 to 6.5-6.9.

Step 8:

Heat the mixture of Step 7 first (at sub-step (a)) to 100° C. for 10 minutes followed second by heating (at sub-step (b)) to 90° C. for 50 minutes, resulting in the formation of a black precipitate solution.

Step 9:

Allow the solution of Step 8 to cool to room temperature (20-25° C.).

Step 10:

Adjust the pH of the suspension of Step 10 to 7.0-7.5.

Step 11:

Increase the final volume of the solution of Step 10 to 13 L by adding the requisite amount of water. This mixture was freeze dried to a powder. The powder can then be formulated into any one of the inventive administrative forms which have already been described herein.

IIIB. THQ Plus Croconic Acid

Step 1:

Create a suspension of a salt of rhodozonic acid and any base that can generate OH anions by mixing both in a 10 L flask with water. The amount of the water is preferably between 1 mL and 10,000 mL (10 L) and more preferably between 300 mL in 1000 mL (1 L). The amount of the rhodozonic acid is preferably between 1 g and 7300 g (7.3 kg) and is more preferably between 100 g in 150 g. The base is taken from the group consisting of KOH, LiOH, NaOH, Mg (OH)$_2$, and Ca (OH)$_2$. The amount of base is preferably between 1 g and 500 g and is more preferably between 100 g and 200 g.

Step 2:

Heat the suspension created in Step 1 to reflux until all rhodizonic acid disodium salt is dissolved and the solution becomes bright yellow, approximately 2 hours. The yellow color is indicative of the formation of croconic acid dipotassium salt ($C_5O_5K_2$, yield=20% by HPLC).

Alternative Initial Step (Alternative to Steps 1 and 2):

Create a solution by adding between 1 g and 1500 g (1.5 kg) and preferably between 15 g and 30 g of croconic acid ($C_5O_5K_2$) to between 1 mL and 10,000 mL of water and more preferably between 300 mL and 1000 mL of water to form a solution. (It should be noted that analogs and equivalents of croconic acid could be substituted for croconic acid.)

Step 3:

Adjust the pH of the solution formed in Step 2 to 9.0-9.4.

Step 4:

Tetrahydroxy-1,4-quinone ($C_6H_4O_6$) preferably in the amount of between 1 g to 2500 g (2.5 kg) and more preferably between 40 g and 80 g is suspended in the solution of Step 3, resulting in a black suspension.

Step 5:

Add water (1.3 L) and heat the suspension of Step 4 to 90° C. for 10 minutes to completely dissolve all materials.

Step 6:

Allow the solution of Step 5 to cool to room temperature (20-25° C.).

Step 7:

Adjust the pH of the suspension of Step 6 to 7.0-7.5.

Step 8:

Increase the final volume of the solution of Step 7 to 13 L by adding the requisite amount of water. This mixture was freeze dried to a powder. The powder can then be formulated into any one of the inventive administrative forms which have already been described herein.

Individual Component Compositions in Inventive Administration Forms

Many of the positive effects of the compositions of the invention may be delivered by treatment using individual components. Specifically, catechol (between 1 g-10,000 g), tetrahydroxyquinone (in its free and sulfited forms) (between 1 g-2500 g), and croconic acid (in its free and sulfited forms) (between 1 g-1500 g) may be individually delivered in the inventive forms described herein, including a time release tablet, or a time release capsule; time release pellets or where the time release pellets are added to other preparations including but not limited to foods and pet foods; tablets or capsules of the non-time release variety including sublingual tablets; gel capsules; microencapsulation; transdermal delivery including a transdermal gel or transdermal patch; a sterile solution prepared for use as an intramuscular or subcutaneous injection, for use as a direct injection into a targeted site, or for intravenous administration; a solution prepared for rectal administration, or for administration through a gastric feeding tube or duodenal feeding tube; or a suppository for rectal administration, topical creams, gels or lotions; an elixir, a tincture, a syrup, an emulsion, or a suspension; or coupled with or administered with known delivery systems including inert carriers or attached to a polymer to form a drug carrier that is designed to reached targeted sites.

EXAMPLE 4

Known Compositions in Inventive Administration Forms

The new administrative forms (formulations) of the invention represent a significant improvement over the oral liquid form of Cantron that has been solely employed for decades as they improve efficacy, dosage compliance, convenience, aesthetics and appeal as they remove the characteristic adverse taste, burning of mouth tissues and other disadvantages. The new forms change the characteristics of the known composition dramatically and these vastly superior properties represent a new and significant invention. The addition of acetogenin or an extract of green tea to the known composition Cantron also represents a significant new invention as it adds synergistic anticancer and/or synergistic antioxidant activity.

New administrative forms of acetogenin also improve the composition by providing chronic dosing to the patient as determined by the Applicant's research. These administrative forms such as time release formulations represent a significant improvement.

4A. Known Composition-Cantron in Inventive Forms and Optionally with the Addition of Acetogenin or an Extract of Green Tea Step 1: React 1200 g Inositol with 2500 cc nitric acid resulting in oxidation products of inositol including tetrahydroxyquinone, rhodizonic acid, triquinoyl, leuconic acid, hexahydrabenzene and traces of inositol.

Step 2: Isolate a percentage of the resultant product of step one to create a suspension of croconic acid. Variations of the known composition have isolated 20% in one version, 40% in another and 100% in yet another variation. For this example we are utilizing 40%. To 40% of the yield of step one solution, add between 60 g and 120 g of potassium hydroxide (KOH). In a water bath, heat at 90° for one hour thereby yielding croconic acid.

Step 3: Combine the yield of step 1 and step 2 in a stainless steel vessel and add 6 liters of distilled water.

Step 4: To the solution of step 3 add between 100 g and 5000 g and more preferably between 500 g and 1800 g of sodium sulfite. Heat the solution at 100° C. for 10 minutes and then heat to 90° C. for an additional 60 minutes, Step 5: To the solution of step 4 add between 1 g and 10,000 g (10 kg) and more preferably in the amount between 300 g and 900 g of catechol ($C_6H_6O_2$). Alternatively, this addition is made to the resultant dry powder after the Final Step and followed by blending.

Optional Step 6: To the solution of step 5 add between 1 g and 10 g and more preferably between 4 g and 8 g of cupric sulfate. Alternatively, this addition is made to the resultant dry powder after the Final Step and followed by blending.

Optional Step 7: To the solution add additional KOH or sodium sulfite as a buffer and/or to increase levels of potassium, sodium and sulfur.

Optional Step 8: To the solution add an acetogenin preferably in the amount of between 0.1 mg and 2000 g (2 kg) and more preferably in the amount of between 3 g and 50 g of pure compound or between 30 g and 500 g of an acetogenin plant extract containing 10% acetogenins. Alternatively, this addition is made to the resultant dry powder after the Final Step and followed by blending.

Optional Step 9: To the solution add an extract of green tea or flavanoids that have similar antioxidant properties such as catechin, epicatechin, epicatechin gallate, epigallocatechin, epigallocatechin gallate, quercitin, rutin, flavone and myricetin, preferably in the amount between 2 grams and 20,000 grams and more preferably between 600 g and 1200 g. Alternatively, this addition is made to the resultant dry powder after the Final Step and followed by blending.

Final Step: Lyophilize (freeze-dry), spray-dry, or vacuum-dry the liquid to create a dry powder. Alternatively, microencapsulation is created directly from the liquid.

Further Optional Steps: The powder can then be formulated into any one of the inventive administrative forms such as a time release tablet, or a time release capsule; time release pellets or where the time release pellets are added to other preparations including but not limited to foods and pet foods; a dry powder or granules or where the dry powder or granules are added to other preparations including but not limited to foods and pet foods; tablets or capsules of the non-time release variety including sublingual tablets; gel capsules; topical creams, gels or lotions; transdermal delivery including a transdermal gel or transdermal patch; a sterile solutions prepared for use as an intramuscular or subcutaneous injection, a direct injection into a targeted site, or for intravenous administration; a suppository for rectal administration; or coupled with or administered with known delivery systems including inert carriers; or attached to a polymer to form a drug carrier designed to reach targeted sites.

4B. Acetogenin in Inventive Forms

An acetogenin in the form of a pure compound, or a botanical containing acetogenin such as Paw Paw or Graviola, in the amount of between 0.1 mg and 2000 g (2 kg) and more preferably in the amount of between 3 g and 30 g is processed into a dry powder or granules by known methods. The powder can then be formulated into any one of the inventive administrative forms such as a time release tablet, or a time release capsule; time release pellets or where the time release pellets are added to other preparations including but not limited to foods and pet foods; transdermal delivery including a transdermal gel or transdermal patch; a sterile solutions prepared for use as an intramuscular or subcutaneous injection, a direct injection into a targeted site, or for intravenous administration; a solution prepared for rectal administration, or for administration through a gastric feeding tube or duodenal feeding tube; a suppository for rectal administration; or coupled with or administered with known delivery systems including inert carriers or attached to a polymer to form a drug carrier designed to reach targeted sites.

EXAMPLE 5

Effectiveness of the Composition

Figure 3:
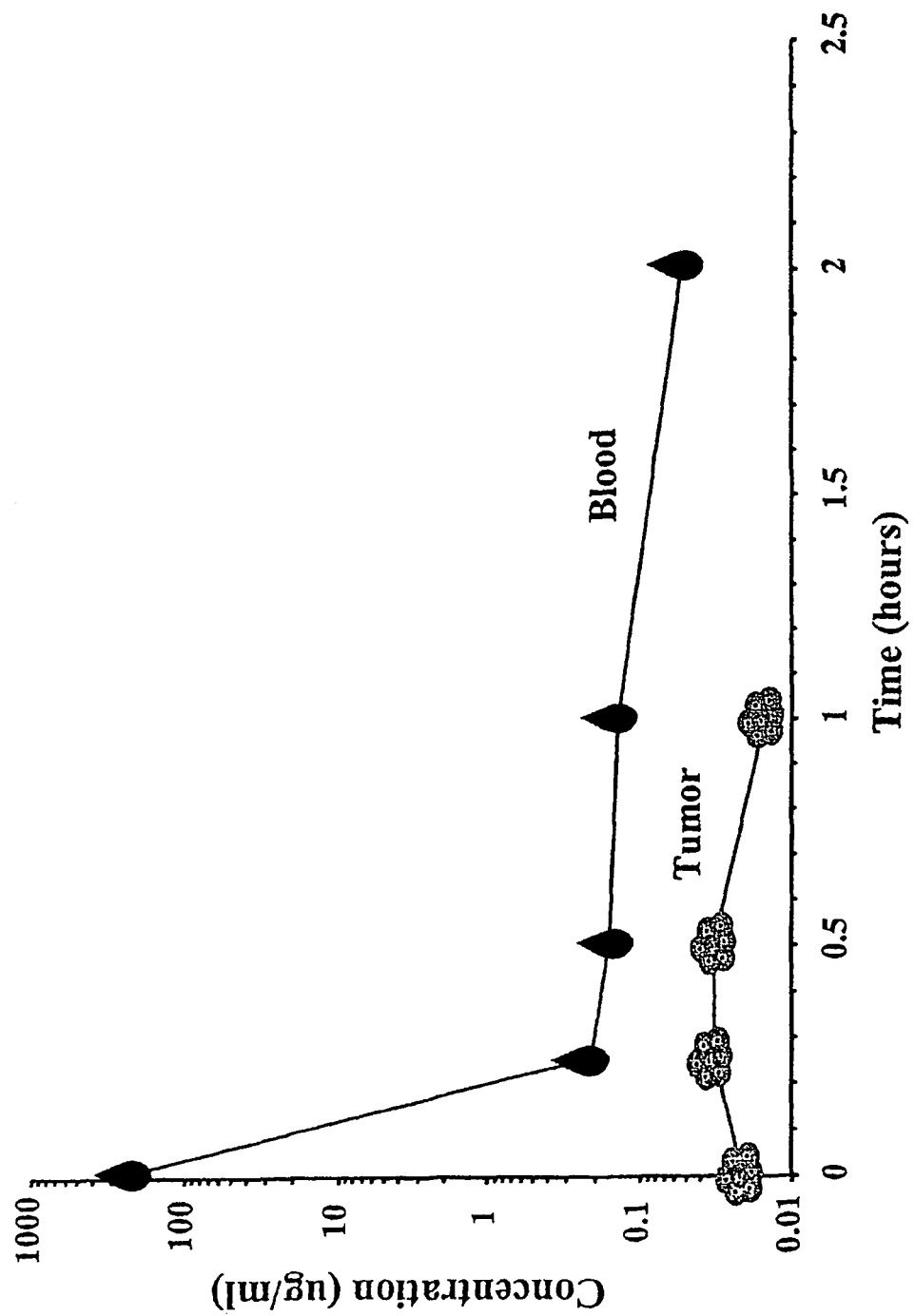
FIG. 3 is a graph demonstrating pharmacokinetics of the levels of active ingredient after a single oral dose of the composition of the present invention.

The time-release kinetics of the composition of the present invention are set forth in FIG. 2 which shows percentage release along the Y-axis and time along the X-axis. As shown, release exceeds 90% after 12 hours. Release of 100% is achieved after 18 hours. FIG. 3 illustrates the levels of active ingredient after a single oral ingestion of the composition of the present invention. Concentration is shown on the Y-axis and time (in hours) is shown on the X-axis.

Figure 4:
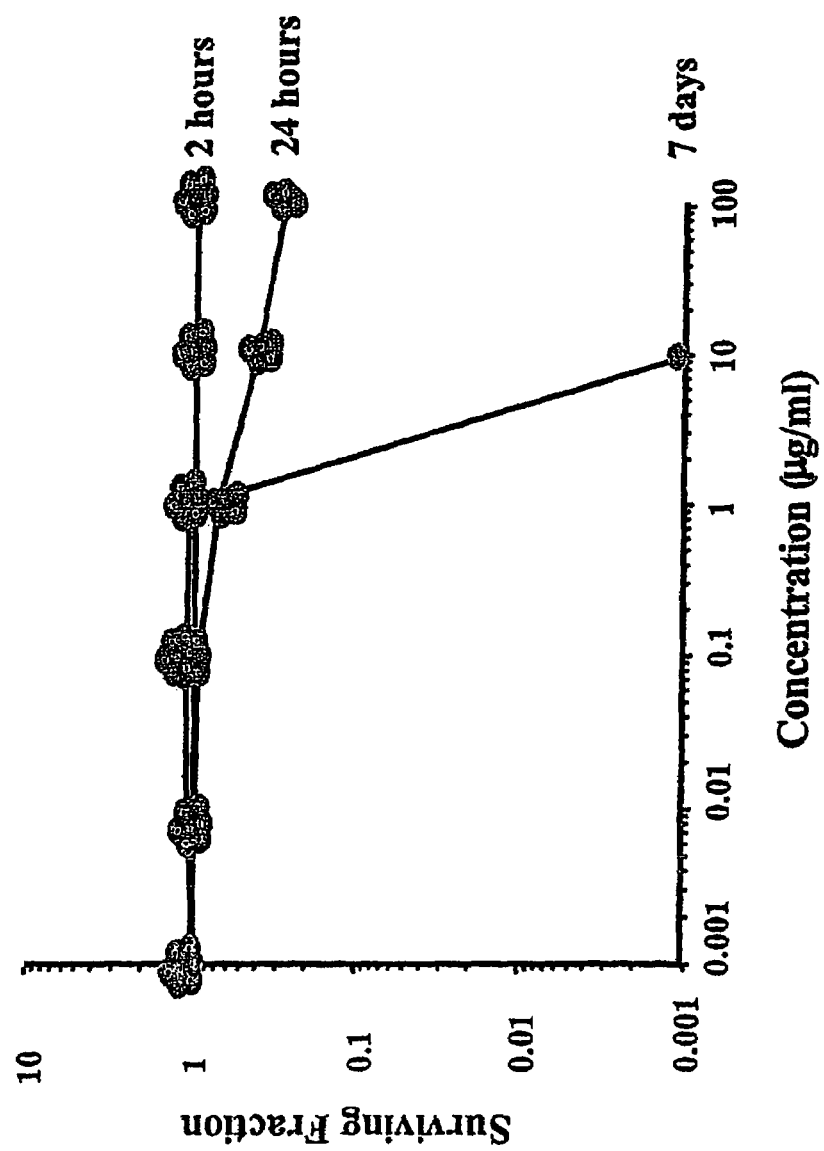
FIG. 4 is a graph that shows the concentration and effect of the tumor-killing composition of the present invention over time.

In addition to its high-antioxidant concentration, the composition of the present invention has demonstrated significant anti-cancer effects. The composition provides a tumor-killing approach to resolution of a broad variety of cancers. The concentration of the tumor-killing composition over time is shown in FIG. 4. According to this graph, the surviving fraction of cancer cells (shown in the Y-axis) versus concentration (shown in the X-axis) is illustrated. The exposure is generally ineffective over two hours but begins to provide maximum effect over twenty-four hours. The concentration is clearly effective at seven days.

EXAMPLE 6

Antioxidant Evaluation

Dozens of compounds and compositions were prescreened in an attempt to improve the overall antioxidant properties of the known composition. Some of the individual components of Cantron were also tested in order to determine which ingredients are responsible for Cantron's antioxidant properties and subsequent to the Applicant's initial findings, to determine which components caused the antioxidant inhibition he discovered. To verify the Applicant's internal results the following compositions were sent to Brunswick Laboratories, and tested for their free radical scavenging abilities against peroxyl lipophilic, peroxyl hydrophilic, hydroxyl, peroxynitrite, and SOD radicals utilizing their standard testing procedures:
1. Cantron® (New Millennium Version) (NM) (Known Composition),
2. Catechol,
3. THQ,
4. THQ disulfite,
5. Croconic Acid,
6. Green Tea Extract,
7. Catechol (35.1%), THQ disulfite (56%), Croconic Acid (8.9%) (percentages are weight to weight),
8. Catechol (34.5%), THQ (8.9%), Green Tea Extract (56.6%) (percentages are weight to weight).
9. Cantron® (Advanced Scientific Version) (ASV) (This new formulation uses 20.4% catechol as opposed to 12.7% in the NM version).

Peroxyl radical scores are measured in the ORAC test (Oxygen Radical Absorption Capacity). Hydroxyl Radicals are tested in the HORAC test (Hydroxyl Radical Absorption Capacity). Peroxynitrite Radicals are tested in the NORAC test (Peroxynitrite Radical Absorption Capacity). Superoxide Radicals are measured in the SOD test (Superoxide Radical Absorption Capacity).

Located in Wareham, Mass., Brunswick Laboratories maintains a state of the art facility with highly skilled scientists. Brunswick serves the nutraceutical, pharmaceutical, food and cosmetic industries. Their antioxidant team developed proprietary high throughput technologies in antioxidant screening and has accumulated the world's largest antioxidant database on a wide variety of natural product compounds. Their expertise has made them a leader in antioxidant activity profiles. See U.S. Pat. No. 7,132,296 regarding the automated ORAC assay.

The ORAC test measures the antioxidant activity against peroxyl radicals by determining how many peroxyl free radicals can be absorbed by a given antioxidant as compared to the vitamin E analog-Trolox. The result is expressed as micromoles of Trolox equivalent per liter (TE/L) for liquid formulations and Trolox equivalent per gram (TE/g) for dry powders. Brunswick tested the Applicant's compounds for antioxidant activity against both hydrophilic and lipophilic peroxyl radicals as expressed in the ORAC total (see table 7). The ORAC tests (Brunswick Test numbers A101, A102, and A103) were based on the method of Huang D. et al (2002) *Journal of Agricultural Food Chemistry*, 50: 4437-4444; Ou B. et al (2001) *Journal of Agricultural and Food Chemistry*, 49(10): 4619-4626; and Huang D. et al (2002) *Journal of Agricultural and Food Chemistry*, 50(7): 1815-1821.

The HORAC test (Brunswick test number A104) measures the activity of a given antioxidant against hydroxyl radicals. Applicant's compounds and compositions were tested based on the method of Ou B. et al (2002) *Journal of Agricultural and Food Chemistry*, 50: 2772-2777; and compared to the test standard, caffeic acid. The result is expressed as micromoles of caffeic acid equivalent per liter (CAE/L) for liquid formulations and caffeic acid equivalent per gram (CAE/g) for dry powders.

Applicant's compounds and compositions were tested by the SORAC test (Brunswick test #106), which measures the activity of a given antioxidant against Superoxide radicals. The tests were conducted based on the method of Zhao et al (1999) *Journal of Agricultural and Food Chemistry*, (1999), 47: 2537-2543. The calibration standard was SOD and was expressed as a unit SOD equivalent per liter (unitsSODeq/L) for liquid formulations and unit SOD equivalent per gram (unitsSODeq/g) for dry powders.

Applicant's compounds and compositions were tested by the NORAC test (Brunswick test # A 105), which measures the activity of a given antioxidant against peroxynitrite radicals. NORAC tests were based on the method of Chung H. et al (2001) *Journal Agricultural of Food Chemistry*, 49: 3614-3621. Scores are expressed in micromoles of trolox equivalent per liter (TE/L) for liquid formulations and Trolox equivalent per gram (TE/g) for dry powders.

The following compositions (1-9) were tested for their free radical scavenging ability in the ORAC (hydrophilic, lipophilic and total ORAC), HORAC, NORAC and SORAC assays.
1. Cantron® New Millennium Version (NM)—contains 12.7% catechol (Known Composition)
2. Cantron® Advanced Scientific Version (ASV)—contains 20.4% catechol
3. Catechol (Pyrocatechol)
4. THQ
5. THQ disulfite
6. Croconic Acid
7. Green Tea Extract
8. Catechol (35.1%) THQ disulfite (56%), Croconic Acid (8.9%)
9. Catechol (34.5%), THQ (8.9%), Green Tea Extract (56.6%)

Scores provided by Brunswick Labs were compiled in Table 1 and ranked from the highest score to the lowest SCORE for each free radical species it was tested on.

TABLE 1

Ranking: Antioxidant Scores

COMPOSITION
NUMBER    COMPOSITION

ORAC TOTAL (Brunswick Test # A103) - measure of the total scavenging ability of PEROXYL hydro and PEROXYL lipo radicals expressed in micromoles TE/g (TE = trolox equivalent). For comparison purposes, Cantron ® oral liquid scores (compositions 1 & 2) were converted from TE/L to TE/g.

| | | TOTAL ORAC SCORE |
|---|---|---|
| 3 | Catechol | 73,161 |
| 9 | Catechol, Green Tea, THQ | 26,769 |
| 8 | Catechol, THQ, Croconic Acid | 26,501 |
| 7 | Green Tea Extract | 11,025 |

TABLE 1-continued

Ranking: Antioxidant Scores

| COMPOSITION NUMBER | COMPOSITION | |
|---|---|---|
| 2 | Cantron ® (ASV) | 10,163 |
| 1 | Cantron ® NM (Known Composition) | 4,299 |
| 4 | THQ | 1,508 |
| 6 | Croconic Acid | 1,106 |
| 5 | THQ disulfite | 314 |

ORAC hydro (Brunswick Test # A101) - measure of the scavenging ability of PEROXYL hydro radicals expressed in micromoles TE/g (TE = trolox equivalent). For comparison purposes, Cantron ® oral liquid scores (compositions 1 & 2) were converted from TE/L to TE/g.

| COMPOSITION NUMBER | COMPOSITION | ORAC hydro SCORE |
|---|---|---|
| 3 | Catechol | 48,479 |
| 9 | Catechol, Green Tea, THQ | 25,291 |
| 8 | Catechol, THQ, Croconic Acid | 17,605 |
| 7 | Green Tea Extract | 11,007 |
| 2 | Cantron ® (ASV) | 9,560 |
| 4 | THQ | 1,507 |
| 6 | Croconic Acid | 1,106 |
| 5 | THQ disulfite | 295 |
| 1 | Cantron ® NM (Known Composition) | Not Provided |

ORAC lipo (Brunswick Test # A102) - measure of the scavenging ability of PEROXYL lipo radicals expressed in micromoles TE/g (TE = trolox equivalent). For comparison purposes, Cantron ® oral liquid scores (compositions 1 & 2) were converted from TE/L to TE/g.

| COMPOSITION NUMBER | COMPOSITION | ORAC lipo SCORE |
|---|---|---|
| 3 | Catechol | 24,682 |
| 8 | Catechol, THQ, Croconic Acid | 8,896 |
| 9 | Catechol, Green Tea, THQ | 1,478 |
| 2 | Cantron ® (ASV) | 604 |
| 5 | THQ disulfite | 19 |
| 7 | Green Tea Extract | 18 |
| 4 | THQ | 1 |
| 6 | Croconic Acid | 0 |
| 1 | Cantron ® NM (Known Composition) | Not Provided |

HORAC (Brunswick Test # A104) - measure of the scavenging ability of HYDROXYL radicals expressed in micromoles CAE/g (CAE = Caffeic Acid equivalent). For comparison purposes, Cantron ® oral liquid scores (compositions 1 & 2) were converted from CAE/L to CAE/g.

| COMPOSITION NUMBER | COMPOSITION | HORAC SCORE |
|---|---|---|
| 3 | Catechol | 5,572 |
| 9 | Catechol, Green Tea, THQ | 4,598 |
| 8 | Catechol, THQ, Croconic Acid | 2,436 |
| 7 | Green Tea Extract | 2,035 |
| 2 | Cantron ® (ASV) | 1,406 |
| 1 | Cantron ® NM (Known Composition) | 268 |
| 4 | THQ | 129 |
| 6 | Croconic Acid | 19 |
| 5 | THQ disulfite | 8 |

NORAC (Brunswick Test # A105) - measure of the scavenging ability of PEROXYNITRITE radicals expressed in micromoles TE/g (TE = trolox equivalent). For comparison purposes, Cantron ® oral liquid scores (compositions 1 & 2) were converted from TE/L to TE/g.

| COMPOSITION NUMBER | COMPOSITION | NORAC SCORE |
|---|---|---|
| 3 | Catechol | 2,593 |
| 9 | Catechol, Green Tea, THQ | 1,952 |
| 7 | Green Tea Extract | 1,693 |
| 2 | Cantron ® (ASV) | 633 |
| 8 | Catechol, THQ, Croconic Acid | 554 |
| 4 | THQ | 438 |
| 5 | THQ disulfite | 69 |
| 6 | Croconic Acid | 1 |
| 1 | Cantron ® NM (Known Composition) | Not Provided |

SORAC (Brunswick Test # A106) - measure of the scavenging ability of SUPEROXIDE radicals expressed in unitsSODeq/g (SODeq = superoxide dismutase equivalent). For comparison purposes, Cantron ® oral liquid scores (compositions 1 & 2) were converted from unitsSODeq/L to units SODeq/g.

| COMPOSITION NUMBER | COMPOSITION | SOD SCORE |
|---|---|---|
| 7 | Green Tea Extract | 358,000 |
| 9 | Catechol, Green Tea, THQ | 269,000 |
| 3 | Catechol | 159,000 |
| 4 | THQ | 145,000 |
| 2 | Cantron ® (ASV) | 36,000 |
| 8 | Catechol, THQ, Croconic Acid | 16,000 |
| 5 | THQ disulfite | 240 |
| 6 | Croconic Acid | 0 |
| 1 | Cantron ® NM (Known Composition) | Not Provided |

With respect to Table 1, Scores of compositions that include acetogenin do not change significantly and thus are not included in Table 1.

Tables 2-5 illustrate whether the aggregate of the individual ingredients in the various compositions have inhibitive, additive or synergistic effects upon various free radical species and whether the inventive compositions and active compounds have inferior, equal or superior properties to the known composition (Cantron® NM). Aggregate scores are compiled by adding the actual scores of all active ingredients in the compositions and are compared to the actual scores of the composition. All scores within a 10% margin (plus or minus) are considered to be an additive effect. Less than 10% are considered inhibitive effects and greater than 10% represents a synergistic effect.

The data presented in Table 2 demonstrates a huge and unexpected inhibitive effect on peroxyl, hydroxyl and superoxide radicals, which is apparently caused by some unknown compound or compounds in Cantron. To improve the antioxidant properties of the Cantron formula, the inhibitive compounds needed to be isolated and eliminated. The most active antioxidant ingredients also needed to be isolated and tested in order to further improve the formulation. No published scores on the individual compounds were found, thus it was imperative to discover the antioxidant properties of the individual compounds by conducting the tests described herein.

TABLE 2

Measure of the Actual Antioxidant Scores of Cantron NM (Known Composition) in Comparison to the Aggregate Scores of its Individual Components For comparison purposes, the oral liquid was converted from a measure of liters to grams.

| RADICAL TYPE | AGGREGATE SCORE | ACTUAL SCORE | DIFFERENCE | RESULT | CONCLUSION |
|---|---|---|---|---|---|
| Peroxyl-total | 9,550 | 4,299 | [−5,251] | Inhibitive | There is an unexpected 55% inhibitive effect from some unknown component(s) in Cantron |
| Hydroxyl | 720 | 268 | [−452] | Inhibitive | There is an unexpected 63% inhibitive effect from some unknown component(s) in Cantron |
| Peroxynitrite | 387 | 389 | +2 | Additive | There is no inhibition from any known component(s) in Cantron |
| Superoxide | 20,510 | 17,668 | [−2,842] | Inhibitive | There is an unexpected 12% inhibitive effect from some unknown component(s) compounds in Cantron |

The data presented in Table 3 demonstrates the superiority of catechol as a single active ingredient composition, in comparison to the known composition (Cantron). The data further demonstrates the surprising and unexpected result that Catechol contains the majority of the antioxidant activity in Cantron. The data also demonstrates that catechol has extremely high scores on all radicals tested. Most impressive is the unexpected high scores on both the hydrophilic and lipophilic peroxyl radical, as most antioxidants are only effective on just one of these types.

TABLE 3

Comparison of the Antioxidant Scores of Catechol as a Single Active Ingredient Composition to Cantron ® NM (Known Composition) on Various Species of Free Radicals

| RADICAL TYPE | CANTRON ® NM SCORE/ ASV SCORE | CATECHOL SCORE | CONCLUSION |
|---|---|---|---|
| Peroxyl-total | 4,299/ 10,163 | 73,161 | The Catechol composition is 1702% more effective than Cantron NM. Conversely, Cantron NM is only 5.88% as effective. |
| Peroxyl-hydro | Not Available/ 9,560 | 48,479 | Extremely high score. No Cantron NM score to compare; however, it is still 507% more effective than the improved Cantron ASV and conversely ASV is only 19.71% as effective. |
| Peroxyl-lipo | Not Available/ 604 | 24,682 | Extremely high score. No Cantron NM score to compare; however, it is still 4086.4% more effective than the improved Cantron ASV and conversely ASV is only 2.44% as effective. |
| Hydroxyl | 268/ 1,406 | 5,572 | The Catechol composition is 2,079% more effective than Cantron NM. Conversely, Cantron NM is only 4.8% as effective. |

TABLE 3-continued

Comparison of the Antioxidant Scores of Catechol as a Single Active Ingredient Composition to Cantron ® NM (Known Composition) on Various Species of Free Radicals

| RADICAL TYPE | CANTRON ® NM SCORE/ ASV SCORE | CATECHOL SCORE | CONCLUSION |
|---|---|---|---|
| Peroxynitrite | Not Available/ 633 | 2,593 | Extremely high score. No Cantron NM score to compare; however, it is still 409.63% more effective than the improved Cantron ASV and conversely, ASV is only 24.41% as effective. |
| Superoxide | Not Available/ 36,000 | 159,000 | Extremely high score. No Cantron NM score to compare; however, it is still 441.66% more effective than the improved Cantron. ASV. Conversely, ASV is only 22.64% as effective |

Regarding Tables 3, 4, and 5, where indicated, Cantron ® NM (known composition) Scores are not available for some of the antioxidant assays and in the absence of such score, Cantron ® ASV is utilized in its place. ASV is a modified version of the known NM composition and it contains more of the most active ingredient catechol. Scores of the known composition on the missing assays would be expected to be much lower than ASV. For example, ASV scores on hydroxyl radicals are 5 times higher than NM. And more than 2 times better on peroxyl radicals.

Table 4 demonstrates that the inventive composition of catechol, THQ disulfite and croconic acid is superior to the known composition (Cantron) on all free radical species with the exception of superoxide. Due to the applicant's discovery of inhibition upon peroxyl and hydroxyl radicals by unknown in Cantron, inhibition was expected for this composition as well. Surprisingly, however, this table demonstrates that this composition solved the problem of the known composition by possessing an unexpected additive effect on peroxyl$_{hydro}$ and peroxyl$_{lipo}$ radicals and an even more powerful synergistic effect on hydroxyl radicals. However, powerful inhibitive effects on peroxynitrite and superoxide radicals were also discovered. Therefore, the composition needed to be further improved by finding the right combination of active antioxidant ingredients that do not suppress the antioxidant activity of certain radical species, and thereby capable of boosting scores even further.

TABLE 4

Comparison of the Antioxidant Scores of the FIRST PREFERRED COMPOSITION: Catechol, THQ disulfite and Croconic Acid (and optionally an acetogenin), to the Aggregate Scores of its Individual Components, and to the Known Composition-Cantron.

| RADICAL TYPE | AGGREGATE SCORE | ACTUAL SCORE | DIFFERENCE | RESULT | CONCLUSION |
|---|---|---|---|---|---|
| Peroxyl-total | 25,918 | 26,501 | +583 | Additive | There is a slight synergistic effect (2.2%) on total peroxyl radicals, which is within the margin of error and thus considered to be an additive effect. This composition is 617% more effective than Cantron. Conversely, Cantron is only 16% as effective. The score for this composition with acetogenin added is 24,646. |
| Peroxyl-hydro | 17,244 | 17,605 | +361 | Additive | There is a slight synergistic effect (2%) on peroxyl hydro radicals, which is within the margin of error and thus considered to be an additive effect. Cantron NM scores for peroxyl |

TABLE 4-continued

Comparison of the Antioxidant Scores of the FIRST PREFERRED COMPOSITION:
Catechol, THQ disulfite and Croconic Acid (and optionally an acetogenin), to the
Aggregate Scores of its Individual Components, and to the Known Composition-Cantron.

| RADICAL TYPE | AGGREGATE SCORE | ACTUAL SCORE | DIFFERENCE | RESULT | CONCLUSION |
|---|---|---|---|---|---|
| | | | | | hydro radicals are not available thus no direct comparison can be made. It is still far superior to the improved ASV which has a score of 9,560 |
| Peroxyl-lipo | 8,664 | 8,896 | +232 | Additive | There is a slight synergistic effect (2.68%) on peroxyl lipo radicals, which is within the margin of error and thus considered to be an additive effect. Cantron NM scores for peroxyl lipo radicals are not available thus no direct comparison can be made. It is still far superior to the improved ASV which has a score of 604. |
| Hydroxyl | 1,962 | 2,436 | +474 | Synergistic | There is an unexpected 24% synergistic effect on hydroxyl radicals. This composition is 909% more effective than Cantron NM. Conversely, Cantron is only 11% as effective. The HORAC score for this composition with acetogenin added is 2,266 |
| Peroxynitrite | 952 | 554 | [−398] | Inhibitive | There is an unexpected 41.81% inhibitive effect on peroxynitrite radicals. Cantron NM scores for peroxynitrite radicals are not available thus no direct comparison can be made. It is slightly inferior to the improved ASV which has a score of 633. |
| SOD | 55,954 | 16,000 | [−39,954] | Inhibitive | There is an unexpected 71.41% inhibitive effect on super oxide radicals. Cantron NM scores for superoxide radicals are not available thus no direct comparison can be made. It is slightly inferior to the improved ASV which has a score of 36,000. |

Table 5 demonstrates that the composition of catechol, Green Tea Extract and THQ (the second preferred composition) further solves the problems of the inhibitive effects upon peroxyl, hydroxyl and superoxide radicals that are inherent in the known composition (cantron) by virtue of possessing unexpected synergistic properties on hydroxyl and peroxyl-hydro radicals, and unexpected additive effects upon peroxynitrite and superoxide radicals. The antioxidant scores on all free radical species tested are far superior to Cantron. This composition of the invention is also much improved over the first preferred composition insofar as it solves that composition's problem of possessing extreme inhibitive properties on peroxynitrite and superoxide radicals (compare superoxide and Peroxynitrite values to Table 4). The second preferred composition replaces the inhibition of peroxynitrite and superoxide radicals observed with the first preferred composition with strong additive effects instead. The second preferred composition is also far superior to the first preferred composition on four of the five free radical species tested. Equally important is the surprising fact that the second preferred composition is even more effective than the catechol composition itself on superoxide radicals.

TABLE 5

Comparison of the Antioxidant Scores of the SECOND PREFERRED COMPOSITION: Catechol, THQ and Green Tea Extract (and optionally an acetogenin), to the Aggregate Scores of its Individual Components, to the Known Composition-Cantron, and to the FIRST PREFERRED COMPOSITION.

| RADICAL TYPE | AGGREGATE SCORE | ACTUAL SCORE | DIFFERENCE | RESULT | CONCLUSION |
|---|---|---|---|---|---|
| Peroxyl-Total | 31,615 | 26,769 | [−4,846] | Inhibitive | There is an 11.81% inhibitive effect on total peroxyl radicals, due to the powerful inhibitive effect on peroxyl lipo radicals. This composition is 623% more effective than Cantron. Conversely, Cantron is only 16.01% as effective. Furthermore, this composition is as effective (1% better score) than the first preferred composition. |
| Peroxyl-hydro | 23,089 | 25,291 | +2,202 | Synergistic | There is an unexpected synergistic effect (9.53%) on peroxyl hydro radicals. This composition is 144% more effective than the first preferred composition. Conversely, the first preferred composition is only 69.61% as effective. |
| Peroxyl-Lipo | 8,534 | 1,478 | [−7,056] | Inhibitive | There is a powerful 577% inhibitive effect on peroxyl lipo radicals. This composition is 16.61% less effective than the first preferred composition. Conversely, the first preferred composition is 602% more effective. |
| Hydroxyl | 3,086 | 4,598 | +1,512 | Synergistic | There is an unexpected 50% synergistic effect on hydroxyl radicals. This composition is 1716% more effective than Cantron. Conversely, Cantron is only 5.82% as effective. Furthermore, this composition is 189% more effective than the first preferred composition. Conversely the first preferred composition is 52.98% as effective. |
| Peroxynitrite | 1,892 | 1,952 | [+60] | Additive | There is a slight synergistic effect (3.17%) on peroxynitrite radicals which is within the margin of error and thus considered to be an additive effect. This composition is 501.80% more effective than Cantron. Conversely, Cantron is only 19.92% as effective. Furthermore, this composition is 352.35% better than the first preferred composition. Conversely, the first preferred composition is 28.35% as effective. |
| Superoxide | 270,388 | 269,000 | [−1,388] | Additive | There is a slight inhibitive effect (.05%) on superoxide radicals, which is within the margin of error, thus considered to be an additive effect. This composition is 1523% more effective than Cantron. Conversely Cantron is only 6.57% as effective. Further more, this composition is 1681% better than the first preferred composition and conversely the first preferred composition is 5.95% as effective. Of additional importance, this is the only score that is superior to the catechol composition. |

EXAMPLE 7

Anti-Rheumatic Factor

The effect of Cantron on Lupus was tested in MRL lpr/lpr Mouse Model:

Lupus is an autoimmune disorder in which a patient's normal antibodies no longer recognize "self" and begin reacting and breaking down a patient's own tissues. This disease is recognized as not just a single disease, but rather a syndrome of a variety of disorders of which some will be more prominent than others.

MRL lpr/lpr mice are an established murine model of this disease that shares many of the same symptoms present in human disease. One group of male MRL lpr/lpr mice freely drank liquid Cantron (diluted 1:200 in water to mimic human daily consumption) while the other group of MRP lpr/lpr mice (control) drank normal water. Both groups were followed until death from the effects of lupus.

The following effects of Cantron on the course of ultimate death from lupus were observed:
 a) Cantron ingestion was without any problems. Thus, Cantron-treated mice drank the same amount of water as the control group and there was no obvious toxicity observed (i.e. the Cantron-treated mice ultimately died with lupus at about the same time as the untreated control mice).
 b) The Cantron-treated mice looked better than the control group (i.e. they had less hair loss and matting of their fur that are indicative of less lupus-induced stress).
 c) The levels of both increased lymph node size and rheumatoid factor were consistently lower in the Cantron-treated mice than in the untreated control mice.
 d) Upon autopsy, there were fewer lupus-induced inflammatory cells in the kidneys of Cantron-treated mice than in the untreated controls.

In summary, Cantron had a measurable and ameliorative effect on some of the parameters (see above) of lupus-induced disease in the MRP lpr/lpr mouse model when compared to an untreated cohort of MRP lpr/lpr mice.

EXAMPLE 8

Time Release Mechanics of the Inventive Compositions

Time-release pellets and capsules were created utilizing Hydroxypropyl Methylcellulose and Shellac as polymers along with organic sucrose, and silicon dioxide as a flow agents and absorbents, and talc as lubricant and filler.

Type: Controlled Release—Dissolves Continuously Over 12 Hours

Dissolution Broad Specification:
 1 Hour: 10%-40%
 4 Hours: 35%-75%
 8 Hours: 70%-95%
 12 Hour: Not less than 85%

For freeze-dried Cantron® (New Millennium version used) in time-release capsule form, the actual measurement is:
 1 Hour 35.75%
 4 Hour 73.85%
 8 Hour 91.27%
 12 Hour 98.63%

Time-Release Tablets were created utilizing Methocel K15 and Ethocel as polymers along with microcrystalline cellulose as an excipient and binder, silicon dioxide as a flow agent and absorbent, and magnesium stearate as filler and lubricant.

Type: Slow Release—Dissolves Continuously Over 12 Hours

Dissolution Broad Specification:
 1 Hour: 10%-40%
 4 Hours: 35%-75%
 8 Hours: 70%-95%
 12 Hour: Not less than 85%

For this composition: catechol (34.5%), THQ (8.9%), green tea extract (56.6%) in time-release tablet form (weight to weight), the actual measurement is:
 1 Hour 39%
 4 Hours 72.5%
 8 Hours 80%
 12 Hours 90.4%

EXAMPLE 9

$IC_{50}$ Assays

Concentration-cell number studies ($IC_{50}$ assay) were carried out utilizing 12 separate compositions (numbered 1-12 below) against 13 different cancer cell lines (see Table 6). These cells are grown in 5 ml culture medium (RPMI-1640+ 15% Bovine Calf serum containing 1% penicillin-streptomycin, and 1% Glutamine) at 37° C. and 5% $CO_2$ at a starting concentration of $5 \times 10^4$ cells/T25 flask. On day 3, cells are exposed to different concentrations of the drug. Flasks are incubated for 120 h (5 d) in a 5% $CO_2$ incubator at 37° C. and the cells harvested with trypsin, washed once with Hanks Balanced Salt Solution (HBSS) and re-suspended in HBSS containing 0.08% Trypan Blue. Both viable and dead cells are counted using a hemocytometer. Viable cell numbers are normalized to an untreated control and plotted as a function of drug concentration. The IC50 value is determined using Prism 4.0.

Cell Lines utilized in $IC_{50}$ Assays: HCT-116 human colon cancer cells, H125 Lung Cancer, MCF-7, Breast Cancer, MDA-235 Breast Cancer, LNCaP Prostate Cancer, OVAR-5 Ovarian Cancer, U251N Brain Cancer Sarcoma 180, Panc 01Pancreatic Cancer, CCRF-CEM Leukemia, HEP-G2 Liver Cancer, L1210 Leukemia, Colon 38 Colon Cancer.

The following compositions (1-12) were tested against all 13 cell lines with the exception of compositions 11 & 12 which were only tested on HCT-116 human colon cancer cells:
 1. Cantron (New Millennium Version)
 2. Catechol
 3. Acetogenin
 4. THQ
 5. Green Tea Extract
 6. Catechol (95.23%), Acetogenin (4.762%)
 7. Catechol (37.9%), Green Tea Extract (62.1%)
 8. Catechol (35.1%) THQ disulfite (56%), Croconic Acid (8.9%)
 9. Catechol (34.5%), THQ (8.9%), Green Tea Extract (56.6%)
 10. Catechol (32.86%), THQ (8.48%), Green Tea Extract (53.9%), Acetogenin (4.76%)
 11. Catechol (33.43%), THQ disulfite (53.3%), Croconic Acid (8.48%), Acetogenin (4.76%)
 12. Cantron (95.23%), Acetogenin (4.762%)

The results of the completed $IC_{50}$ Assays on compositions 1-10 are compiled in Table 6 and are expressed in µg/ml or ng/ml. The results of compositions 11-12 are shown in tables 7 & 8.

TABLE 6

IC50 Values for Cantron ® NM (1) and Inventive Compositions 2-10

| Cell Line | 1. | 2. | 3. | 4. | 5. | 6. | 7. | 8. | 9. | 10. |
|---|---|---|---|---|---|---|---|---|---|---|
| HCT-116 Colon Cancer | 19.7 µg/ml | 2.8 µg/ml | 2.0 ng/ml | 17 µg/ml | 76 µg/ml | 10 ng/ml | 5.1 µg/ml | 7.0 µg/ml | 5.9 µg/ml | 2.3 ng/ml |
| H125 Lung Cancer | 30 µg/ml | 2.1 µg/ml | 1.4 ng/ml | 53 µg/ml | 61 µg/ml | 14 ng/ml | 11 µg/ml | 6.6 µg/ml | 6.1 µg/ml | 32 ng/ml |
| MCF-7 Breast Cancer | 25 µg/ml | 2.2 µg/ml | 1.3 ng/ml | 5.9 µg/ml | 60 µg/ml | 18 ng/ml | 11 µg/ml | 3.2 µg/ml | 1.4 µg/ml | 36 ng/ml |
| MDA-235 Breast Cancer | 28 µg/ml | 3.0 µg/ml | 1.3 ng/ml | 5.8 µg/ml | 54 µg/ml | 17 ng/ml | 11 µg/ml | 10 µg/ml | 4.6 µg/ml | 11 ng/ml |
| LNCaP Prostate Cancer | 32 µg/ml | 1.7 µg/ml | 5.0 ng/ml | 54 µg/ml | 55 µg/ml | 22 ng/ml | 1.3 µg/ml | 4.5 µg/ml | 5.0 µg/ml | 16 ng/ml |
| OVAR-5 Ovarian Cancer | 23 µg/ml | 3.2 µg/ml | 1.8 ng/ml | 28 µg/ml | 13 µg/ml | 36 ng/ml | 10 µg/ml | 9.0 µg/ml | 5.5 µg/ml | 31 ng/ml |
| U251N Brain Cancer | 23 µg/ml | 2.2 µg/ml | 1.2 ng/ml | 8.0 µg/ml | 52 µg/ml | 18 ng/ml | 3.7 µg/ml | 6.1 µg/ml | 4.3 g/ml | 23 ng/ml |
| Sarcoma 180 | 23 µg/ml | 1.9 µg/ml | 1.2 ng/ml | 51 µg/ml | 62 µg/ml | 18 ng/ml | 4.1 µg/ml | 7.4 µg/ml | 5.8 µg/ml | 12 ng/ml |
| Panc 01 Pancreatic Cancer | 25 µg/ml | 1.7 µg/ml | .41 ng/ml | 24 µg/ml | 52 µg/ml | 430 ng/ml | 13 µg/ml | 9 µg/ml | 5.2 µg/ml | 220 ng/ml |
| CCRF-CEM Leukemia | 13 µg/ml | 2.1 µg/ml | 5.2 ng/ml | 7.0 µg/ml | 6.2 µg/ml | 25 ng/ml | 2.2 µg/ml | 2.1 µg/ml | 1.3 µg/ml | 32 ng/ml |
| HEP-G2 Liver Cancer | 12 µg/ml | 2.6 µg/ml | 2.2 ng/ml | 8.5 µg/ml | 16 µg/ml | 19 ng/ml | 2.8 µg/ml | 9.2 µg/ml | 2.8 µg/ml | 12 ng/ml |
| L1210 Leukemia | 20 µg/ml | 1.9 µg/ml | 13 ng/ml | 49 µg/ml | 46 µg/ml | 21 ng/ml | 20 µg/ml | 6.7 µg/ml | 5.3 µg/ml | 27 ng/ml |
| Colon 38 Colon Cancer | 25 µg/ml | 2.2 µg/ml | .19 ng/ml | 19 µg/ml | 6.2 µg/ml | 19 ng/ml | 2.7 µg/ml | .62 µg/ml | 1.8 µg/ml | 18 ng/ml |
| AVG. | 23 µg/ml | 2.3 µg/ml | 2.8 ng/ml | 25 µg/ml | 43 µg/ml | 51 ng/ml | 7.5 µg/ml | 6.3 µg/ml | 4.2 µg/ml | 36 ng/ml |

Table 7 compares the $IC_{50}$ scores of the inventive composition of catechol, THQ, croconic acid & acetogenin (composition 11) to Cantron and demonstrates that this inventive composition is many times more effective than the Cantron composition on HCT-116 human cancer cell lines.

TABLE 7

IC50 Values for HCT-116 Colon Cancer: Comparison Chart of the Inventive Composition: Catechol, THQ, Croconic Acid, Acetogenin (First Preferred Composition; composition 11)

| Cell Line | Actual Score | Cantron Score | Conclusion |
|---|---|---|---|
| HCT-116 Colon Cancer | 0.13 µg/ml | 19.7 µg/ml | 152 times lower than Cantron NM |

IC50 Result Chart: Mathematical measure of inferior, equal or superior properties in relation to Cantron NM.

Table 8 compares the $IC_{50}$ scores of the inventive composition of Cantron & acetogenin (composition 12) to Cantron NM and demonstrates that this inventive composition is many times more effective than the Cantron composition on HCT-116 human cancer cell lines. Therefore, the addition of acetogenin has a powerful anticancer effect on Cantron.

TABLE 8

IC50 Values for HCT-116 Colon Cancer: Comparison Chart of the Inventive Composition: Cantron plus Acetogenin (composition 12)

| Cell Line | Actual Score | Cantron Score | Conclusion |
|---|---|---|---|
| HCT-116 Colon Cancer | 0.03 µg/ml | 19.7 µg/ml | 656.67 times lower than Cantron NM |

IC50 Result Chart: Mathematical measure of inferior, equal or superior properties in relation to Cantron NM.

Table 9 compares the cytotoxicity $IC_{50}$ values of the various inventive compositions to known nutraceuticals and known anti-cancer pharmaceuticals; in HCT-116 human colon cancer cell lines. Accordingly, the compositions of the present invention demonstrate high cytotoxicity when compared with anticancer pharmaceuticals and nutraceuticals. Included in this comparison, catchol, the most active ingredient of the known composition Cantron®, demonstrates a cytotoxicity of 2.8 µg/ml compared with the known anticancer pharmaceuticals 5-fluorouracil, cis-platinum, adriamycin, vincristine and taxol, demonstrating increasing cytotoxicy. This experimentally determined value of 2.8 µg/ml is consistent with the calculated value of 2.5 µg/ml based on: the observed cytotoxicity of 19.7 µg/ml for Cantron® adjusted for percentage of weight of catechol in Cantron® (The score of Cantron (19.7) was multiplied by 12.7% representing the percentage of catechol by weight in the formula, yielding the value of 2.5019.) Further in comparison to this activity of catechol, the nutraceuticals in the forms of alpha-lipoic acid, vitamins E and C, green tea, and grapeseed, show decreasing cytoxicity.

TABLE 9

IC50 Values for HCT-116 Colon Cancer: A comparison of Cantron ® NM and the Various Inventive Compositions to Known Pharmaceuticals and Nutraceuticals.

| Composition | IC50 (µg/ml) |
|---|---|
| Taxol | 0.0002 |
| Composition 3 | 0.002 |
| Composition 10 | 0.0023 |
| Vincristine | 0.005 |
| Composition 6 | 0.01 |
| Composition 12 | 0.03 |
| Adriamycin | 0.03 |
| cis-Platinum | 0.10 |
| Composition 11 | 0.15 |
| 5-Fluorouracil | 0.15 |
| Composition 2 | 2.8 |
| Composition 7 | 5.1 |
| Composition 9 | 5.9 |
| Composition 8 | 7.0 |
| Composition 4 | 17.0 |
| Composition 1 | 19.7 |
| Composition 5 | 76.0 |
| Alpha-lipoic acid | >100 |
| Vitamin E | >100 |
| Vitamin C | >100 |
| Green Tea | >100 |
| Grape Seed | >100 |

Table 10 compares the $IC_{50}$ scores of catechol as an individual composition (composition 2) to Cantron. Conclusion: Catechol as an individual anticancer component is superior to the known composition Cantron on all 13 cell lines tested; ranging from 3.69 times better to 18.82 times more effective, and an average of 10.35 times more effective.

TABLE 10

IC50 for Various Cancer Cell Lines: Comparison Chart for the Composition: Catechol in Inventive Administrative Forms (composition 2)

| Cell Line | Actual Score | Cantron Score | Conclusion |
|---|---|---|---|
| HCT-116 Colon Cancer | 2.8 µg/ml | 19.7 µg/ml | 7.04 times lower than Cantron |

TABLE 10-continued

IC50 for Various Cancer Cell Lines: Comparison Chart for the Composition: Catechol in Inventive Administrative Forms (composition 2)

| Cell Line | Actual Score | Cantron Score | Conclusion |
|---|---|---|---|
| H125 Lung Cancer | 2.1 µg/ml | 30 µg/ml | 14.29 times lower than Cantron |
| MCF-7 Breast Cancer | 2.2 µg/ml | 25 µg/ml | 11.36 times lower than Cantron |
| MDA-235 Breast Cancer | 3.0 µg/ml | 28 µg/ml | 9.33 times lower than Cantron |
| LNCaP Prostate Cancer | 1.7 µg/ml | 32 µg/ml | 18.82 times lower than Cantron |
| OVAR-5 Ovarian Cancer | 3.2 µg/ml | 23 µg/ml | 3.69 times lower than Cantron |
| U251N Brain Cancer | 2.2 µg/ml | 23 µg/ml | 10.45 times lower than Cantron |
| Sarcoma 180 | 1.9 µg/ml | 23 µg/ml | 12.11 times lower than Cantron |
| Panc 01 Pancreatic Cancer | 1.7 µg/ml | 25 µg/ml | 14.71 times lower than Cantron |
| CCRF-CEM Leukemia | 2.1 µg/ml | 13 µg/ml | 6.19 times lower than Cantron |
| HEP-G2 Liver Cancer | 2.6 µg/ml | 12 µg/ml | 4.61 times lower than Cantron |
| L1210 Leukemia | 1.9 µg/ml | 20 µg/ml | 10.52 times lower than Cantron |
| Colon 38 Colon Cancer | 2.2 µg/ml | 25 µg/ml | 11.36 times lower than Cantron |

IC50 Result Chart: Mathematical measure of inferior, equal or superior properties in relation to Cantron NM.

Table 11 compares $IC_{50}$ values of the inventive composition of catechol and acetogenin (composition 6) to Cantron and demonstrates that the catechol/acetogenin composition is many times more effective than the Cantron composition. The aggregate $IC_{50}$ scores of the individual components catechol and acetogenin were also calculated and compared to the actual scores of the composition in order to determine whether these compounds have inhibitive, additive or synergistic effects. Conclusion: The combination of catechol and acetogenin has unexpected synergistic effects on all 13 cancer cell lines tested, ranging from 3.77 times to 7,999 times lower than the additive scores, averaging 723.10 times better than the additive score. This composition is more efficacious than Cantron on all 13 cell lines tested; ranging from 58.14 times to 2,142.86 times more efficacious, and averaging 1,175.05 times more efficacious. The combination is also more efficacious than catechol on all 13 cell lines tested; ranging from 3.95 to 280 times more efficacious, and averaging 119.54 times more efficacious.

TABLE 11

IC50 for Various Cancer Cell Lines: Comparison Chart for the Inventive Composition: Catechol, Acetogenin (composition 6)

| Cell Line | Aggregate Score | Actual Score | Score Differential | Result | Conclusion |
|---|---|---|---|---|---|
| HCT-116 Colon Cancer | 2,666.69 ng/ml | 10 ng/ml | −2,656.79 ng/ml | S | Extreme Synergistic Effect: 266.68 times lower than the additive (aggregate) score. It is 1,970 times lower than Cantron; and 280 times lower than catechol. |
| H125 Lung Cancer | 2,000.06 ng/ml | 14 ng/ml | −1,986.06 ng/ml | S | Extreme Synergistic Effect: 142.86 times lower than the additive (aggregate) score. It is 2,142.86 times lower than Cantron and 150 times lower than catechol. |

TABLE 11-continued

IC50 for Various Cancer Cell Lines: Comparison Chart for the
Inventive Composition: Catechol, Acetogenin (composition 6)

| Cell Line | Aggregate Score | Actual Score | Score Differential | Result | Conclusion |
|---|---|---|---|---|---|
| MCF-7 Breast Cancer | 2,095.30 ng/ml | 18 ng/ml | −2,077.30 ng/ml | S | Extreme Synergistic Effect: 116.41 times lower than the additive (aggregate) score. It is 1,388.89 times lower than Cantron and 122.22 times lower than catechol. |
| MDA-235 Breast Cancer | 2884.44 ng/ml | 17 ng/ml | −2867.44 ng/ml | S | Extreme Synergistic Effect: 169.67 times lower than the additive (aggregate) score. It is 1,647.06 times lower than Cantron and 176.47 times lower than catechol. |
| LNCaP Prostate Cancer | 1,618.81 ng/ml | 22 ng/ml | −1,596.81 ng/ml | S | Extreme Synergistic Effect: 73.58 times lower than the additive (aggregate) score. It is 1,454.55 times lower than Cantron and 77.27 times lower than catechol. |
| OVAR-5 Ovarian Cancer | 3,047.53 ng/ml | 36 ng/ml | −3,011.53 ng/ml | S | Extreme Synergistic Effect: 84.65 times lower than the additive (aggregate) score. It is 638.89 times lower than Cantron and 88.88 times lower than catechol. |
| U251N Brain Cancer | 2,095.18 ng/ml | 18 ng/ml | −2077.18 ng/ml | S | Extreme Synergistic Effect: 116.40 times lower than the additive (aggregate) score. It is 1,277.78 times lower than Cantron and 122.22 times lower than catechol. |
| Sarcoma 180 | 1,809.46 ng/ml | 18 ng/ml | −1791.46 ng/ml | S | Extreme Synergistic Effect: 100.53 times lower than the additive (aggregate) score. It is 1,277.78 times lower than Cantron and 105.56 times lower than catechol. |
| Panc 01 Pancreatic Cancer | 1,609.07 ng/ml | 430 ng/ml | −1,189.07 ng/ml | S | Powerful Synergistic Effect: 3.77 times lower than the additive (aggregate) score. It is 58.14 times lower than Cantron and 3.95 times lower than catechol. |
| CCRF-CEM Leukemia | 1,999.75 ng/ml | .25 ng/ml | −1,999.50 ng/ml | S | Extreme Synergistic Effect: 7,999 times lower than the additive (aggregate) score. It is 520 times lower than Cantron and 84 times lower than catechol. |
| HEP-G2 Liver Cancer | 2,476.29 ng/ml | 19 ng/ml | −2,457.29 ng/ml | S | Extreme Synergistic Effect: 130.33 times lower than the additive (aggregate) score. It is 631.58 times lower than Cantron and 136.84 times lower than catechol. |
| L1210 Leukemia | 1,810.14 ng/ml | 21 ng/ml | −1,789.14 ng/ml | S | Extreme Synergistic Effect: 86.20 times lower than the additive (aggregate) score. It is 952.38 times lower than Cantron and 90.84 times lower than catechol. |
| Colon 38 Colon Cancer | 2095.23 ng/ml | 1.4 ng/ml | −2,093.83 ng/ml | S | Extreme Synergistic Effect: 110.28 times lower than the additive (aggregate) score. It is 1,315.79 times lower than Cantron and 115.79 times lower than catechol. |

IC50 Result Chart: Mathematical measure of inhibitive, additive or synergistic effects and of inferior, equal or superior properties in relation to Cantron NM and other inventive anti-cancer compositions.
I = Inhibitive Effect;
A = Additive Effect;
S = Synergistic Effect.

Table 12 compares the $IC_{50}$ values of the inventive composition of catechol, THQ & Green Tea Extract to Cantron NM and demonstrates that this inventive composition is many times more effective than the Cantron composition. The aggregate $IC_{50}$ scores of the individual components catechol, THQ & Green Tea Extract (composition 9) were also calculated and compared to the actual scores of the composition in order to determine whether these compounds have inhibitive, additive or synergistic effects. It is concluded that the combination of catechol, THQ and Green Tea Extract has surprising synergistic effects on all 13 cancer cell lines tested, ranging from 1.99 to 25.17 lower than the additive score, and averaging 6.74 times lower. The $IC_{50}$ values are even lower than the most active ingredient catechol, on 3 separate cell lines; further demonstrating the powerful synergistic effects of the components. The average $IC_{50}$ value is 1.47 times lower than catechol. The composition is superior to Cantron on all 13 cell lines tested; ranging from 3.34 times to 17.86 times more efficacious, with an average of 6.39. This composition is also superior to the composition of catechol, THQ, & croconic acid by an average of 1.36 times and is more efficacious on 11 of the 13 cell lines tested.

TABLE 12

IC50 for Various Cancer Cell Lines: Comparison Chart for the INVENTIVE COMPOSITION: Catechol, THQ, Green Tea Extract (composition 9)

| Cell Line | Aggregate Score | Actual Score | Score Differential | Result | Conclusion |
|---|---|---|---|---|---|
| HCT-116 Colon Cancer | 45.5 µg/ml | 5.9 µg/ml | −39.6 µg/ml | S | Powerful Synergistic Effect: It is 7.71 times lower than the additive (aggregate score). It is 3.34 times lower than Cantron; and 1.19 times lower than the composition of catechol, THQ and croconic acid. |
| H125 Lung Cancer | 39.97 µg/ml | 6.1 µg/ml | −33.87 µg/ml | S | Powerful Synergistic Effect: It is 6.55 times lower than the additive (aggregate score). It is 3.87 times lower than Cantron; and 1.08 times lower than the composition of catechol, THQ and croconic acid. |
| MCF-7 Breast Cancer | 35.2 µg/ml | 1.4 µg/ml | −33.84 µg/ml | S | Powerful Synergistic Effect: It is 25.17 times lower than the additive (aggregate score) and even 1.57 times lower than the most active ingredient catechol (1.4 µg/ml to 2.2 µg/ml). It is 17.86 times lower than Cantron and 2.29 times lower than the composition of catechol, THQ and croconic acid. |
| MDA-235 Breast Cancer | 32.12 µg/ml | 4.6 µg/ml | −27.52 µg/ml | S | Synergistic Effect: It is 6.98 times lower than the additive (aggregate score), 6.09 times lower than Cantron; and 2.17 times lower than the composition of catechol, THQ and croconic acid. |
| LNCaP Prostate Cancer | 46.98 µg/ml | 5.0 µg/ml | −41.98 µg/ml | S | Synergistic Effect: It is 9.40 times lower than the additive (aggregate score), and 6.4 times lower than Cantron. |
| OVAR-5 Ovarian Cancer | 10.95 µg/ml | 5.5 µg/ml | −5.45 µg/ml | S | Synergistic Effect: It is 1.99 times lower than the additive (aggregate score). It is 4.18 times lower than Cantron; and 1.64 times lower than the composition of catechol, THQ and croconic acid. |
| U251N Brain Cancer | 30.9 µg/ml | 4.3 µg/ml | −26.6 µg/ml | S | Powerful Synergistic Effect: It is 7.19 times lower than the additive (aggregate score). It is 5.3 times lower than Cantron; and 1.42 times lower than the composition of catechol, THQ and croconic acid. |

TABLE 12-continued

IC50 for Various Cancer Cell Lines: Comparison Chart for the
INVENTIVE COMPOSITION: Catechol, THQ, Green Tea Extract (composition 9)

| Cell Line | Aggregate Score | Actual Score | Score Differential | Result | Conclusion |
|---|---|---|---|---|---|
| Sarcoma 180 | 40.29 µg/ml | 5.8 µg/ml | −34.49 µg/ml | S | Powerful Synergistic Effect: It is 6.95 times lower than the additive (aggregate score). It is 3.97 times lower than Cantron; and 1.28 times lower than the composition of catechol, THQ and croconic acid. |
| Panc 01 Pancreatic Cancer | 32.15 µg/ml | 5.2 µg/ml | −2.05 µg/ml | S | Synergistic Effect: 6.18 times lower than the additive (aggregate score), 5.38 times lower than Cantron; and 1.73 times lower than the composition of catechol, THQ and croconic acid. |
| CCRF-CEM Leukemia | 4.84 µg/ml | 1.3 µg/ml | −3.54 µg/ml | S | Powerful Synergistic Effect: 3.72 times lower than the additive (aggregate score), and it is even 1.61 times lower than the active ingredient with the lowest score-catechol. It is 10 times lower than Cantron; and 1.61 times lower than the composition of catechol, THQ and croconic acid. |
| HEP-G2 Liver Cancer | 10.71 µg/ml | 2.8 µg/ml | −7.91 µg/ml | S | Powerful Synergistic Effect: 3.82 times lower than the additive (aggregate score), 4.29 times lower than Cantron; and 3.29 times lower than the composition of catechol, THQ and croconic acid. |
| L1210 Leukemia | 31.05 µg/ml | 5.3 µg/ml | −25.75 µg/ml | S | Powerful Synergistic Effect: 5.86 times lower than the additive (aggregate score), 3.77 times lower than Cantron; and 1.26 times lower than the composition of catechol, THQ and croconic acid. |
| Colon 38 Colon Cancer | 5.96 µg/ml | 1.8 µg/ml | −4.16 µg/ml | S | Powerful Synergistic Effect: 3.31 times lower than the additive (aggregate score), 13.89 times lower than Cantron; and 1.2 times lower than catechol-the active ingredient with the lowest score. |

IC50 Result Chart: Mathematical measure of inhibitive, additive or synergistic effects and of inferior, equal or superior properties in relation to Cantron NM and other inventive anti-cancer compositions.
I = Inhibitive Effect;
A = Additive Effect;
S = Synergistic Effect Table 13 compares the $IC_{50}$ values of the inventive composition of catechol, THQ, Green Tea Extract & acetogenin (composition 10) to Cantron NM and demonstrates that this inventive composition is many times more effective than the Cantron composition. The aggregate $IC_{50}$ scores of the individual components catechol, THQ, Green Tea Extract & acetogenin were also calculated and compared to the actual scores of the composition in order to determine whether these compounds have inhibitive, additive or synergistic effects. It is concluded that the combination of catechol, THQ, Green Tea Extract and acetogenin has surprising synergistic effects on all 13 cancer cell lines tested; ranging from 138.20 to 18,838.30 times lower than the additive score, and averaging 2,487.25 times lower. The composition is superior to Cantron on all 13 cell lines tested ranging from 113.64 times to 8,565.20 times more efficacious, with an average of 1,619.29. It is superior to the composition of catechol, THQ, & croconic acid on all 13 cell lines by an average of 510.28 times lower, ranging from 24.81 to 3,043.47 times better. The IC50 score for this composition with the inclusion of just 1 part of acetogenin per 21 parts, ranges from 23.64 to 2,565.22 times lower than the same composition without acetogenin by an average of 382.08.

TABLE 13

IC50 for Various Cancer Cell Lines: Comparison Chart for the
Inventive Composition: Catechol, THQ, Green Tea Extract, Acetogenin (composition 10)

| Cell Line | Aggregate Score | Actual Score | Score Differential | Result | Conclusion |
|---|---|---|---|---|---|
| HCT-116 Colon Cancer | 43,328.10 ng/ml | 2.3 ng/ml | −43,325.80 ng/ml | S | Extreme Synergistic Effect: It is 18,838 times lower than the additive (aggregate) score. There are synergistic effects upon synergistic effects in play with this composition. Acetogenin adds further synergistic effects to the catechol, THQ and green tea composition, which already has demonstrated powerful synergistic effects of its own (7.71 times lower than the aggregate score). The IC50 score for this composition with the inclusion of just 1 part of acetogenin per 21 parts, is 2,565 times lower than same composition without acetogenin and multiplies the already existing 7.71 times synergistic effect by an additional 2,443 (7.71 × 2,443 = 18,838). This composition is 8,565.2 times lower than Cantron, 1,217.39 times lower than catechol; 43.48 times lower than the preferred composition (catechol, THQ, croconic acid, acetogenin); and 3,043.47 times lower than a composition of catechol, THQ, and croconic acid. It is almost as effective as acetogenin by itself (86%) and by factoring in the greater volume of cancer killing agents (21 times more volume); this composition is 18.3 times better than acetogenin. |
| H125 Lung Cancer | 8,087.16 ng/ml | 32 ng/ml | −8,055.16 ng/ml | S | Extreme Synergistic Effect: It is 252.72 times lower than the additive (aggregate) score. The IC50 score for this composition with the inclusion of just 1 part of acetogenin per 21 parts is 190.63 times lower than same composition without acetogenin. This composition is 937.50 times lower than Cantron, 65.63 times lower than catechol, 206.25 times lower than a composition of catechol, THQ, and croconic acid. |
| MCF-7 Breast Cancer | 33,565.39 ng/ml | 36 ng/ml | −33,529.39 ng/ml | S | Extreme Synergistic Effect: It is 932.37 times lower than the additive (aggregate) score. The IC50 score for this composition with the inclusion of just 1 part of acetogenin per 21 parts is 38.88 times lower than same composition without acetogenin. This composition is 694.44 times lower than Cantron, 61.11 times lower than catechol, and 88.88 times lower than a composition of catechol, THQ, and croconic acid. |
| MDA-235 Breast Cancer | 30,585.54 ng/ml | 11 ng/ml | −30,574.54 ng/ml | S | Extreme Synergistic Effect: It is 2,780.50 times lower than the additive (aggregate) score. The IC50 score for this composition with the inclusion of just 1 part of acetogenin per 21 parts is 418.18 times lower than same composition without acetogenin. This composition is 2,545.45 |

TABLE 13-continued

IC50 for Various Cancer Cell Lines: Comparison Chart for the
Inventive Composition: Catechol, THQ, Green Tea Extract, Acetogenin (composition 10)

| Cell Line | Aggregate Score | Actual Score | Score Differential | Result | Conclusion |
|---|---|---|---|---|---|
| | | | | | times lower than Cantron, 272.73 times lower than catechol, and 909.09 times lower than a composition of catechol, THQ, and croconic acid. |
| LNCaP Prostate Cancer | 34,783.03 ng/ml | 16 ng/ml | −34,767.03 ng/ml | S | Extreme Synergistic Effect: it is 2,173.94 times lower than the additive (aggregate) score. The IC50 score for this composition with the inclusion of just 1 part of acetogenin per 21 parts is 312.50 times lower than same composition without acetogenin. This composition is 2,000.00 times lower than Cantron, 106.25 times lower than catechol, and 281.25 times lower than a composition of catechol, THQ, and croconic acid. |
| OVAR-5 Ovarian Cancer | 10,432.31 ng/ml | 31 ng/ml | −10,401.31 ng/ml | S | Extreme Synergistic Effect: It is 336.53 times lower than the additive (aggregate) score. The IC50 score for this composition with the inclusion of just 1 part of acetogenin per 21 parts is 177.42 times lower than same composition without acetogenin. This composition is 741.94 times lower than Cantron, 103.23 times lower than catechol, and 290.32 times lower than a composition of catechol, THQ, and croconic acid. |
| U251N Brain Cancer | 29,431.06 ng/ml | 23 ng/ml | −29,408.06 ng/ml | S | Extreme Synergistic Effect: It is 1279.61 times lower than the additive (aggregate) score. The IC50 score for this composition with the inclusion of just 1 part of acetogenin per 21 parts is 186.96 times lower than same composition without acetogenin. This composition is 1,000 times lower than Cantron, 95.65 times lower than catechol, and 265.22 times lower than a composition of catechol, THQ, and croconic acid. |
| Sarcoma 180 | 38,367.57 ng/ml | 1.2 ng/ml | −38,355.57 ng/ml | S | Extreme Synergistic Effect: It is 3,197.30 times lower than the additive (aggregate) score. The IC50 score for this composition with the inclusion of just 1 part of acetogenin per 21 parts is 483.33 times lower than same composition without acetogenin. This composition is 967.67 times lower than Cantron, 158.33 times lower than catechol, and 616.67 times lower than a composition of catechol, THQ, and croconic acid. |
| Panc 01 Pancreatic Cancer | 30,622.91 ng/ml | 220 ng/ml | −30,402.91 ng/ml | S | Extreme Synergistic Effect: It is 138.20 times lower than the additive (aggregate) score. The IC50 score for this composition with the inclusion of just 1 part of acetogenin per 21 parts is 23.64 times lower than same composition without acetogenin. This composition is 113.64 times lower than Cantron, 7.73 times lower than catechol, and 40.91 times lower than a composition of catechol, THQ, and croconic acid. |

TABLE 13-continued

IC50 for Various Cancer Cell Lines: Comparison Chart for the
Inventive Composition: Catechol, THQ, Green Tea Extract, Acetogenin (composition 10)

| Cell Line | Aggregate Score | Actual Score | Score Differential | Result | Conclusion |
|---|---|---|---|---|---|
| CCRF-CEM Leukemia | 4,625.59 ng/ml | 32 ng/ml | −4,593.59 ng/ml | S | Extreme Synergistic Effect: is 144.55 times lower than the additive (aggregate) score. The IC50 score for this composition with the inclusion of just 1 part of acetogenin per 21 parts is 40.63 times lower than same composition without acetogenin. This composition is 406.25 times lower than Cantron, 65.63 times lower than catechol, and also 65.63 times lower than a composition of catechol, THQ, and croconic acid. |
| HEP-G2 Liver Cancer | 10,199.38 ng/ml | 12 ng/ml | −10,187.38 ng/ml | S | Extreme Synergistic Effect: It is 849.95 times lower than the additive (aggregate) score. The IC50 score for this composition with the inclusion of just 1 part of acetogenin per 21 parts is 233.33 times lower than same composition without acetogenin. This composition is 1,000 times lower than Cantron, 216.66 times lower than catechol, and also 766.66 times lower than a composition of catechol, THQ, and croconic acid. |
| L1210 Leukemia | 29,573.97 ng/ml | 27 ng/ml | −29,546.97 ng/ml | S | Extreme Synergistic Effect: It is 1,095.33 times lower than the additive (aggregate) score. The IC50 score for this composition with the inclusion of just 1 part of acetogenin per 21 parts is 196.30 times lower than same composition without acetogenin. This composition is 740.74 times lower than Cantron, 70.37 times lower than catechol, and also 24.81 times lower than a composition of catechol, THQ, and croconic acid. |
| Colon 38 Colon Cancer | 5,675.33 ng/ml | 18 ng/ml | −5,657.33 ng/ml | S | Extreme Synergistic Effect: It is 315.30 times lower than the additive (aggregate) score. The IC50 score for this composition with the inclusion of just 1 part of acetogenin per 21 parts is 100 times lower than same composition without acetogenin. This composition is 1,388.89 times lower than Cantron, 122.22 times lower than catechol, and also 34.44 times lower than a composition of catechol, THQ, and croconic acid. |

IC50 Result Chart: Mathematical measure of inhibitive, additive or synergistic effects and of inferior, equal or superior properties in relation to Cantron NM and other inventive anti-cancer compositions.
I = Inhibitive Effect;
A = Additive Effect;
S = Synergistic Effect Table 14 compares the $IC_{50}$ scores of the inventive composition of catechol, THQ & croconic acid (composition 8) to Cantron NM. It is concluded that the composition of Catechol, THQ, and croconic acid is superior to Cantron on all 13 cell lines tested; ranging from 1.3 times to 40.32 times more effective, and averaging 6.78 times more effective.

TABLE 14

IC50 for Various Cancer Cell Lines: Comparison Chart for the Inventive Composition: Catechol, THQ, Croconic Acid (composition 8)

| Cell Line | Actual Score | Cantron Score | Conclusion |
|---|---|---|---|
| HCT-116 Colon Cancer | 7.0 µg/ml | 19.7 µg/ml | 2.81 times lower than Cantron |
| H125 Lung Cancer | 6.6 µg/ml | 30 µg/ml | 4.55 times lower than Cantron |
| MCF-7 Breast Cancer | 3.2 µg/ml | 25 µg/ml | 7.81 times lower than Cantron |
| MDA-235 Breast Cancer | 10 µg/ml | 28 µg/ml | 2.8 times lower than Cantron |
| LNCaP Prostate Cancer | 4.5 µg/ml | 32 µg/ml | 7.11 times lower than Cantron |
| OVAR-5 Ovarian Cancer | 9.0 µg/ml | 23 µg/ml | 2.56 times lower than Cantron |
| U251N Brain Cancer | 6.1 µg/ml | 23 µg/ml | 3.77 times lower than Cantron |
| Sarcoma 180 | 7.4 µg/ml | 23 µg/ml | 3.11 times lower than Cantron |
| Panc 01 Pancreatic Cancer | 9.0 µg/ml | 25 µg/ml | 2.78 times lower than Cantron |
| CCRF-CEM Leukemia | 2.1 µg/ml | 13 µg/ml | 6.19 times lower than Cantron |
| HEP-G2 Liver Cancer | 9.2 µg/ml | 12 µg/ml | 1.3 times lower than Cantron |
| L1210 Leukemia | 6.7 µg/ml | 20 µg/ml | 2.99 times lower than Cantron |
| Colon 38 Colon Cancer | .62 µg/ml | 25 µg/ml | 40.32 times lower than Cantron |

IC50 Result Chart: Mathematical measure of inferior, equal or superior properties in relation to Cantron NM.

Table 15 compares the $IC_{50}$ values of the inventive composition of catechol & Green Tea Extract to Cantron NM and demonstrates that this inventive composition is many times more effective than the Cantron composition. The aggregate $IC_{50}$ scores of the individual components catechol, & Green Tea Extract were also calculated and compared to the actual scores of the composition in order to determine whether these compounds have inhibitive, additive or synergistic effects. It is concluded that the composition of catechol and Green Tea Extract has synergistic effects on 12 of 13 cell lines tested; ranging from 1.46 to 26.77 times lower than the aggregate (additive) score, and averaging 5.81 times lower than the additive score. It is superior to Cantron on 12 of 13 cell lines tested, ranging from 1.3 to 24.62 times more efficacious than Cantron, and averaging 5.46 times better than Cantron.

TABLE 15

IC50 for Various Cancer Cell Lines: Comparison Chart for the Inventive Composition: Catechol, Green Tea Extract

| Cell Line | Aggregate Score | Actual Score | Score Differential | Result | Conclusion |
|---|---|---|---|---|---|
| HCT-116 Colon Cancer | 48.26 µg/ml | 5.1 µg/ml | −43.16 µg/ml | S | Powerful synergistic effect: 3.52 times lower than the aggregate (additive) score. It is 2.73 times more efficacious than Cantron. |
| H125 Lung Cancer | 38.68 µg/ml | 11 µg/ml | −27.68 µg/ml | S | Powerful synergistic effect: 9.47 times lower than the aggregate (additive) score. It is 3.86 times more efficacious than Cantron. |
| MCF-7 Breast Cancer | 38.09 µg/ml | 11 µg/ml | −27.09 µg/ml | S | Powerful synergistic effect: 3.46 times lower than the aggregate (additive) score. It is 2.27 times more efficacious than Cantron. |
| MDA-235 Breast Cancer | 34.67 µg/ml | 11 µg/ml | −23.67 µg/ml | S | Powerful synergistic effect: 3.15 times lower than the aggregate (additive) score. It is 2.55 times more efficacious than Cantron. |
| LNCaP Prostate Cancer | 34.80 µg/ml | 1.3 µg/ml | −33.50 µg/ml | S | Powerful synergistic effect: 26.77 times lower than the aggregate (additive) score. It is 24.62 times more efficacious than Cantron. |
| OVAR-5 Ovarian Cancer | 9.29 µg/ml | 10 µg/ml | (.71) µg/ml | I | Slight inhibitive effect: 1.08 times higher than the aggregate (additive) score. It is 2.3 times more efficacious than Cantron. |
| U251N Brain Cancer | 33.13 µg/ml | 3.7 µg/ml | −29.43 µg/ml | S | Powerful synergistic effect: 8.95 times lower than the aggregate (additive) score. It is 6.21 times more efficacious than Cantron. |

TABLE 15-continued

IC50 for Various Cancer Cell Lines: Comparison Chart for the
Inventive Composition: Catechol, Green Tea Extract

| Cell Line | Aggregate Score | Actual Score | Score Differential | Result | Conclusion |
|---|---|---|---|---|---|
| Sarcoma 180 | 39.22 µg/ml | 4.1 µg/ml | −35.12 µg/ml | S | Powerful synergistic effect: 9.57 times lower than the aggregate (additive) score. It is 5.61 times more efficacious than Cantron. |
| Panc 01 Pancreatic Cancer | 32.94 µg/ml | 13 µg/ml | −19.94 µg/ml | S | Powerful synergistic effect: 2.53 times lower than the aggregate (additive) score. It is 1.3 times less efficacious than Cantron. |
| CCRF-CEM Leukemia | 4.65 µg/ml | 2.2 µg/ml | −2.45 µg/ml | S | Powerful synergistic effect: 2.11 times lower than the aggregate (additive) score. It is 5.91 times more efficacious than Cantron. |
| HEP-G2 Liver Cancer | 10.92 µg/ml | 2.8 µg/ml | −8.12 µg/ml | S | Powerful synergistic effect: 3.9 times lower than the aggregate (additive) score. It is 4.29 times more efficacious than Cantron. |
| L1210 Leukemia | 29.29 µg/ml | 20 µg/ml | −9.29 µg/ml | S | Powerful synergistic effect: 1.46 times lower than the aggregate (additive) score. It is as efficacious as Cantron. |
| Colon 38 Colon Cancer | 4.68 µg/ml | 2.7 µg/ml | −1.98 µg/ml | S | Powerful synergistic effect: 1.73 times lower than the aggregate (additive) score. It is 9.3 times more efficacious than Cantron. |

IC50 Result Chart: Mathematical measure of inhibitive, additive or synergistic effects and of inferior, equal or superior properties in relation to Cantron NM and other inventive anti-cancer compositions.
I = Inhibitive Effect;
A = Additive Effect;
S = Synergistic

EXAMPLE 10

Clonogenic Assays

Figure 5:
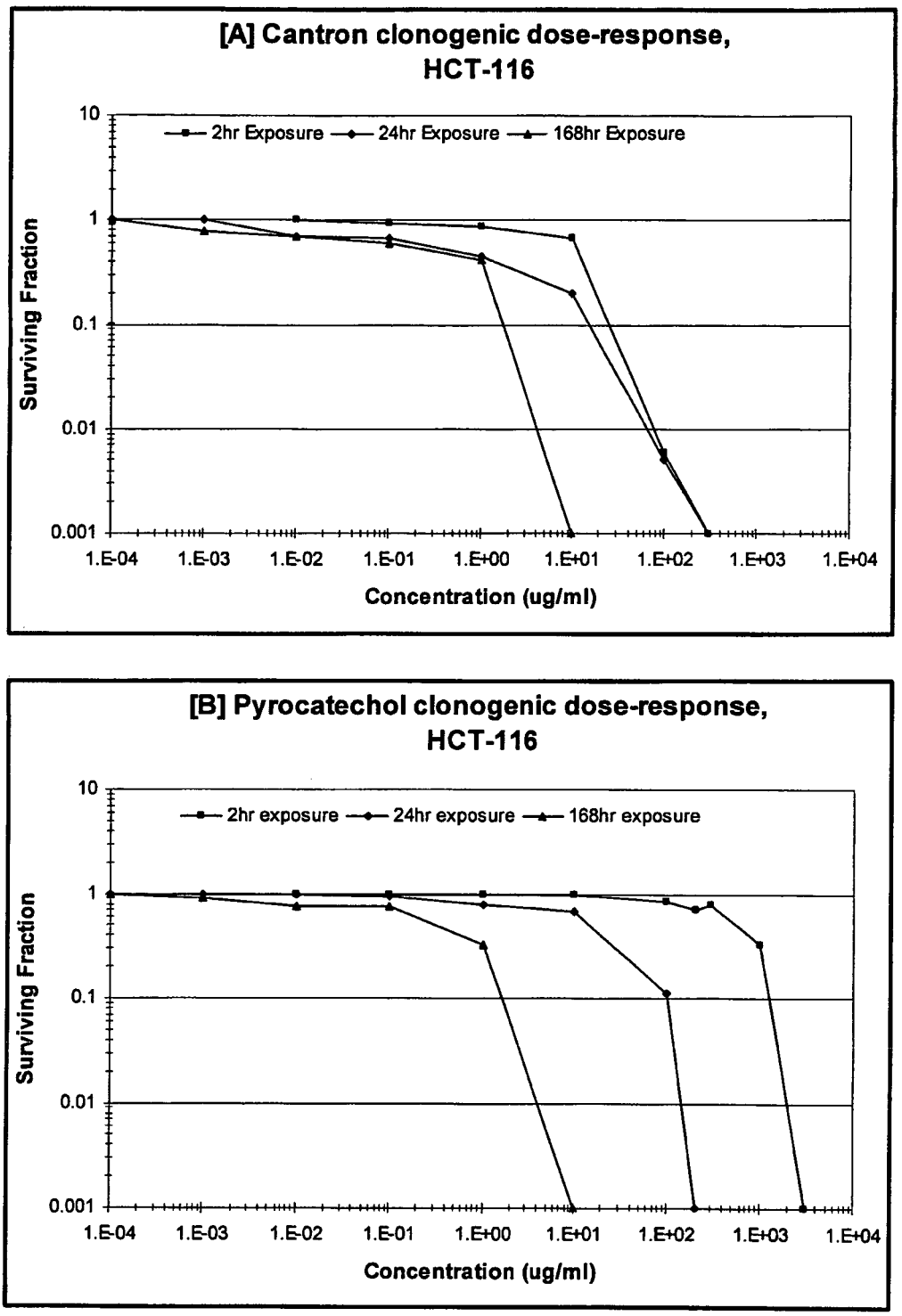
FIG. 5 depicts Cantron & pyrocatechol (catechol) clonogenic dose response in HCT-116 human cancer cell lines.

Cantron & Pyrocatechol (Catechol) Clonogenic Dose Response in HCT-116 Human Cancer Cell Lines:

Cantron & pyrocatechol (catechol) clonogenic dose response in HCT-116 human cancer cell lines were conducted and the data for both compositions shows that the optimal schedule for dosing would be a chronic (time release) exposure (FIG. 5). HCT-116 human colon cancer cells were exposed to Cantron & pyrocatechol (catechol) at the concentrations indicated in FIG. 5. Clonogenic survival of the cells was measured by a standard tissue culture procedure. Exposure of these cells to concentration of up to 10 micrograms/ml had no effect on the survival of the tumor cells. Exposure of the cells for 24 h yielded no effect for concentrations up to 1 microgram/ml and some cell killing (survival=0.1) for 10 micrograms/ml. Surprisingly, extended exposure (168 h in this Figure), yielded dramatic and unexpected cell killing with cell survival at the 0.1 level occurring at 200 picograms/ml, nearly 100.000-fold greater cell killing than found with the 24 h exposure. These results indicate that for any anti-tumor therapeutic effect in vivo Cantron & pyrocatechol would have to be administered chronically, probably in a time release formulation or other preparation which facilitates chronic exposure to cancer cells.

Figure 6:
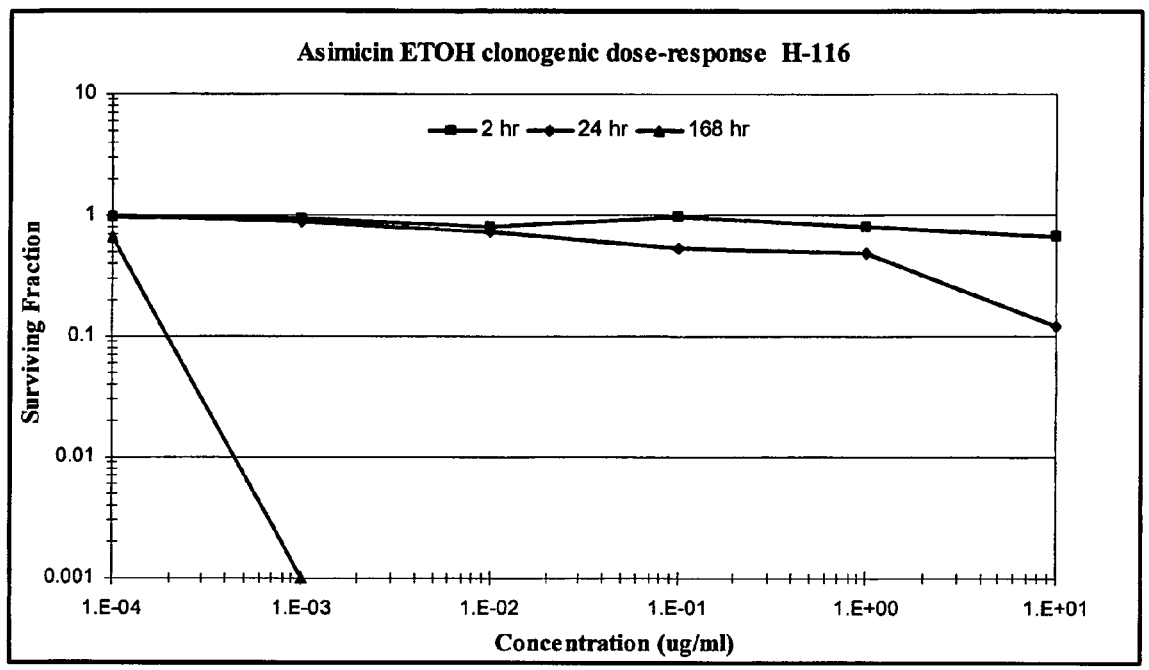
FIG. 6 depicts Asimicin (acetogenin compound) ETOH clonogenic dose response in HCT-116 human cancer cell lines.

Asimicin (Acetogenin Compound) ETOH Clonogenic Dose Response in HCT-116 Human Cancer Cell Lines:

Asimicin (acetogenin compound) ETOH clonogenic dose response in HCT-116 human cancer cell lines were conducted and the data for the acetogenin (asimicin) shows that, like catechol, the optimal schedule for dosing, would be a chronic (time release) exposure (FIG. 6). Asimicin was prepared in ethanol. HCT-116 human colon cancer cells were exposed to Asimicin prepared in ethanol at the concentrations indicated in FIG. 6. Clonogenic survival of the cells was measured by a standard tissue culture procedure. Exposure of these cells to concentration of up to 10 micrograms/ml had no effect on the survival of the tumor cells. Exposure of the cells for 24 h yielded no effect for concentrations up to 1 microgram/ml and some cell killing (survival=0.1) for 10 micrograms/ml. Surprisingly, extended exposure (168 h in FIG. 6), yielded dramatic and unexpected cell killing with cell survival at the 0.1 level occurring at 200 picograms/ml, nearly 100.000-fold greater cell killing than found with the 24 h exposure. These results indicate that for any anti-tumor therapeutic effect in vivo asimicin, and by extension, any cytotoxic acetogenin would have to be administered chronically, probably in a time release formulation or other preparation which facilitates chronic exposure to cancer cells.

Summary:

Many unexpected results were discovered as a result of the Applicant's research and led to many significant improvements to the known composition-Cantron® and its variations most notably Entelev®, Cancell® and Protocel®. In contrast to previous determinations by NCI, FDA and ACS, both Cantron and catechol were found to be efficacious against a wide variety of cancers when those cell lines were chronically exposed to the composition. Acetogenins have been known to have high anticancer activity, but it was not previously known that chronic dosing was required to achieve efficacies. The Applicant's research determined that inventive forms of administration needed to be created for Cantron®, catechol, acetogenin or any combination thereof in order to improve optimum efficacy, and for greater convenience in complying with the stringent chronic dosage requirements without the many disadvantages of the oral liquid. Furthermore, as described herein, it is discovered that catechol is most effective in the inventive time release form as it delivers a constant supply of the ingredient and chronic exposure to free radicals. As the majority of catechol is released in the intestinal tract, it also overcomes known side effects in animal tests including stomach irritation and hyperplasia. The inventive formulations of catechol described herein; are superior to the known forms of catechol which consist of bulk powder or crystals for industrial uses or as one ingredient in the oral liquid Cantron.

Inventive ingredient combinations serve to improve the invention even further. Whether by reduction or elimination of inactive ingredients or by addition of other synergistic compounds, all formulas are far superior to the known composition on all cancer cell lines test. The combination of catechol and acetogenin, and the combination of catechol and an extract of green tea, both have synergistic anticancer properties on all 13 cell lines tested. THQ adds further synergy to the composition of catechol and green tea and acetogenin geometrically compounds the synergistic properties of this composition. In addition, the compositions that contain 1 part acetogenin to 20 parts of other active components are further improved by the creation of substantially higher volumes of anticancer agent over acetogenin alone. Unexpected synergistic and additive antioxidant effects were also achieved with the inventive compositions and all new compositions were superior to the known composition.

In a mouse study, lower rheumatoid factors were observed and demonstrate the invention's effectiveness upon auto-immune diseases.

The invention claimed is:

1. A therapeutic time release composition consisting essentially of:
   (a) catechol;
   (b) an acid selected from the group consisting of croconic acid and sulfites of croconic acid;
   (c) a quinone selected from the group consisting of tetrahydroxy quinone and sulfites of tetrahydroxy quinone; and
   (d) an anti-neoplastic in the form of an acetogenin,
   and wherein said composition is formulated as a time release tablet, a time release capsule, a time release pellet or a time release gel.

2. A food preparation consisting essentially of:
   (a) catechol;
   (b) an acid selected from the group consisting of croconic acid and sulfites of croconic acid;
   (c) a quinone selected from the group consisting of tetrahydroxy quinone and sulfites of tetrahydroxy quinone; and
   (d) an anti-neoplastic in the form of an acetogenin.

3. The composition of claim 1 further including a pharmaceutically acceptable carrier or inert carrier.

4. The composition of claim 1 wherein the anti-neoplastic is a botanical preparation.

5. The composition of claim 4 wherein the botanical preparation comprises components of Paw Paw Tree, Graviola Tree or an extract of said components.

6. A composition of claim 2 which further comprises at least one food ingredient or pet food ingredient.

* * * * *